(12) United States Patent
Coronado et al.

(10) Patent No.: US 10,105,377 B2
(45) Date of Patent: Oct. 23, 2018

(54) COMPOUNDS AND NAIL POLISH (71) Applicant: Anacor Pharmaceuticals, Inc., Palo Alto, CA (US)

(72) Inventors: Dina Coronado, Santa Clara, CA (US); Tejal Merchant, Cupertino, CA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 15/309,408

(22) PCT Filed: Jan. 13, 2015

(86) PCT No.: PCT/US2015/011240
§ 371 (c)(1),
(2) Date: Nov. 7, 2016

(87) PCT Pub. No.: WO2015/171186
PCT Pub. Date: Nov. 12, 2015

(65) Prior Publication Data
US 2017/0216327 A1 Aug. 3, 2017

Related U.S. Application Data (60) Provisional application No. 61/988,897, filed on May 5, 2014.

(51) Int. Cl.
*A61K 31/69* (2006.01)
*A61K 8/73* (2006.01)
*A61Q 3/02* (2006.01)
*A61K 9/00* (2006.01)

(52) U.S. Cl.
CPC .............. *A61K 31/69* (2013.01); *A61K 8/731* (2013.01); *A61K 9/0014* (2013.01); *A61Q 3/02* (2013.01); *A61K 2800/884* (2013.01)

(58) Field of Classification Search
CPC ...................................................... A61K 39/64
See application file for complete search history.

(56) References Cited

U.S. PATENT DOCUMENTS

| 6,231,875 B1 | 5/2001 | Sun et al. |
| 6,391,964 B1 | 5/2002 | Tartaglia |
| 2006/0234981 A1 | 10/2006 | Baker et al. |

FOREIGN PATENT DOCUMENTS

| JP | 2002-509867 A | 4/2002 |
| JP | 2009-526751 A | 7/2009 |
| WO | WO 99/49835 A1 | 10/1999 |
| WO | WO 2007/078340 A2 | 7/2007 |

OTHER PUBLICATIONS

Baker et al (Journal of Medicinal Chemistry, 2006, vol. 49, No. 15, 4447-4450).*
Hui et al (Journal of Pharmaceutical Sciences, vol. 96, No. 10, Oct. 2007).*
Zeicher et al (J Clin Aesthet Dermatol. Sep. 2014; 7(9): 34-36).*

* cited by examiner

*Primary Examiner* — Benjamin J Packard
(74) *Attorney, Agent, or Firm* — Christian M. Smolizza (57) ABSTRACT

Compositions, methods, and kits that deliver a compound, such as 5-fluoro-1,3-dihydro-1-hydroxy-2,1-benzoxaborole, through a keratin substrate are presented.

9 Claims, 1 Drawing Sheet

AN IN VITRO NAIL PENETRATION STUDY WITH EX VIVO HUMAN NAILS DEMONSTRATES THE PENETRATION OF TAVABOROLE TOPICAL SOLUTION, 5% THROUGH NAIL POLISH

Dina Coronado, Sanjay Chanda, Tejal Merchant, Wei Bu, Lee T. Zane; Anacor Pharmaceuticals, Inc., Palo Alto, CA

INTRODUCTION

Onychomycosis is a common infection of the fingernails and toenails which causes nails to become thickened and discolored.[1]

The estimated incidence of onychomycosis is 8-14% but increases with age and may be as high as 50% among those older than 70 years.[2,3]

Tavaborole is a broad-spectrum oxaborole antifungal agent. It is a highly specific protein synthesis inhibitor that targets fungal cytoplasmic leucyl-tRNA synthetase (LeuRS), an aminoacyl-tRNA synthetase.[4] These enzymes play a pivotal role in maintaining and translating the genetic code within fungal DNA. Tavaborole binds to the active editing site and traps tRNA, preventing catalytic turnover and synthesis of leucine-charged tRNAs. In this way, tavaborole inhibits cellular protein synthesis and thus suppresses fungal activity.

In an in vitro permeation model using ex vivo human cadaver fingernails, tavaborole exhibited greater penetration into the nail plate and achieved 250-fold greater quantity through the nail compared with ciclopirox.[5]

As affected individuals may wish to use nail polish to mask the appearance of infected nails, the objective of this study was to evaluate the nail penetration properties of Tavaborole Topical Solution, 5% through nail polish on fingernails obtained from human female cadavers using the Franz finite dose permeation model.[6]

METHODS

Five fingernails from four deceased female donors (N=20) were divided into two treatment groups. Two nails per donor received one coat of a commercial brand of nail polish and two other nails per donor received no nail polish. One nail from each donor served as a non-dosed control.

Each fingernail was mounted on a 7 mm diameter modified Franz diffusion cell and secured in place with silicone glue (Figure 1). Tavaborole Topical Solution, 5% was applied to each nail (except the non-dosed control) once daily for 20 consecutive days using a positive placement pipette calibrated to deliver 12.5 µL/cm² of solution.

Acknowledgement
This study was sponsored by Anacor Pharmaceuticals, Inc., Palo Alto, CA 94043, USA

METHODS (CONT)

Penetration of Tavaborole Topical Solution, 5% was measured by monitoring the rate of appearance of tavaborole in the receptor solution (phosphate buffered saline) bathing the inner surface of the nail.

The receptor solution was collected everyday over the course of the study and analyzed for the presence of tavaborole using a qualified liquid chromatography-tandem mass spectrometry (LC/MS/MS) method.

FIGURE 1

Fingernail mounted on a modified Franz diffusion cell.

RESULTS

The mean (SD) cumulative penetration of tavaborole in the treatment group with nail polish was 3,526 (1,433) µg/cm² compared to 2,661 (1,319) µg/cm² in the group with no nail polish.

The mean cumulative penetration of tavaborole over the 20-day study period is shown in Figure 2.

Although numerically superior, penetration of Tavaborole Topical Solution, 5% through nails with nail polish was not statistically different from penetration through nails without nail polish.

CONCLUSION

These results demonstrate that Tavaborole Topical Solution, 5% was able to penetrate through one coat of a commercial brand of nail polish.

FIGURE 2

Mean Cumulative Penetration of Tavaborole Topical Solution, 5% Across Donors.

REFERENCES

1. Elewski BE. Onychomycosis: pathogenesis, diagnosis, and management. *Clin Microbiol Rev.* 1998;11:415-29.

2. Gupta AK, Jain HC, Lynde CW, et al. Prevalence and epidemiology of onychomycosis in patients visiting physicians' offices: a multicenter Canadian survey of 15,000 patients. *Am Acad Dermatol.* 2000;43(2 Pt 1):244-8.

3. Ghannoum MA, Hajjeh RA, Scher R, et al. A large-scale North American study of fungal isolates from nails: the frequency of onychomycosis, fungal distribution, and antifungal susceptibility patterns. *J Am Acad Dermatol.* 2000;43:641-8.

4. Rock FL, Mao W, Yaremchuk A, et al. An antifungal agent inhibits an aminoacyl-tRNA synthetase by trapping tRNA in the editing site. *Science.* 2007;316:1759-61.

5. Hui X, Baker SJ, Wester RC, et al. In vitro penetration of a novel oxaborole antifungal (AN2690) into the human nail plate. *J Pharm Sci.* 2007;96:2622-31.

6. Franz TJ. The finite dose technique as a valid in vitro model for the study of percutaneous absorption in man. *Curr Probl Dermatol.* 1978;7:58-68.

COMPOUNDS AND NAIL POLISH

CROSS-REFERENCE TO RELATED APPLICATION

This application is a National Stage of International Patent Application No. PCT/US2015/011240 filed Jan. 13, 2015 and published as WO 2015/171186 A1, which claims priority to U.S. Provisional Application No. 61/988,897 filed May 5, 2014, the entire contents of which applications is incorporated herein for all purposes by this reference.

BACKGROUND OF THE INVENTION

Onychomycosis is a common infection of the fingernails and toenails which causes nails to become thickened and discolored. Elewski B E. Onychomycosis: pathogenesis, diagnosis, and management. *Clin Microbiol Rev.* 1998; 11:415-29. The estimated incidence of onychomycosis is 8-14% but increases with age and may be as high as 50% among those older than 70 years. Gupta A K, Jain H C, Lynde C W, et al. Prevalence and epidemiology of onychomycosis in patients visiting physicians' offices: a multicenter Canadian survey of 15,000 patients. *Am Acad Dermatol.* 2000; 43(2 Pt 1):244-8; Ghannoum M A, Hajjeh R A, Scher R, et al. A large-scale North American study of fungal isolates from nails: the frequency of onychomycosis, fungal distribution, and antifungal susceptibility patterns. *J Am Acad Dermatol.* 2000; 43:641-8.

Tavaborole is a broad-spectrum oxaborole antifungal agent. It is a highly specific protein synthesis inhibitor that targets fungal cytoplasmic leucyl-tRNA synthetase (LeuRS), an aminoacyl-tRNA synthetase. Rock F L, Mao W, Yaremchuk A, et al. An antifungal agent inhibits an aminoacyl-tRNA synthetase by trapping tRNA in the editing site. *Science.* 2007; 316:1759-6 These enzymes play a pivotal role in maintaining and translating the genetic code within fungal DNA. Tavaborole binds to the active editing site and traps tRNA, preventing catalytic turnover and synthesis of leucine-charged tRNAs. In this way, tavaborole inhibits cellular protein synthesis and thus suppresses fungal activity. In an in vitro permeation model using ex vivo human cadaver fingernails, tavaborole exhibited greater penetration into the nail plate and achieved 250-fold greater quantity through the nail compared with ciclopirox. Hui X, Baker S J, Wester R C, et al. In vitro penetration of a novel oxaborole antifungal (AN2690) into the human nail plate. *J Pharm Sci.* 2007; 96:2622-31.

The impact of diseases of the nail, such as onychomycosis, on an individual are not insignificant. Lubeck et al. Quality of Life Research, Vol. 8, p. 121-129 (1999). Sufferers of fingernail dystrophy may limit activities which require fine touch such as typing or playing a musical instrument, and sufferers of toenail dystrophy may experience pain or discomfort walking, standing, and exercising. Sufferers of onychomycosis have reported issues such as paresthesia, loss of fine touch, pain and problems retrieving small objects, as well as psychosocial effects connected with nail appearance such as embarrassment and social withdrawal. Drake et al., J. Am. Acad. Dermatol. 1998; 38: 702-704.

Surprisingly, it has been discovered that delivery of 5-halogen benzoxaboroles through a mammalian nail can be increased by placing at least one additional layer of material over the mammalian nail before the application of the 5-halogen benzoxaborole to the mammalian nail. The advantages provided by compositions, methods, and kits utilizing this finding, as well as others, are described herein.

SUMMARY OF THE INVENTION

In an aspect, the invention provides a method of delivering a compound through a keratin substrate, comprising: a) applying a nail polish to the keratin substrate, thus forming a coated nail; and b) applying to the coated nail, a pharmaceutical formulation comprising a pharmaceutically acceptable excipient and the compound, wherein the compound has the structure:

wherein $R^1$ is a halogen, or a pharmaceutically acceptable salt, solvate, or hydrate thereof, thereby delivering the compound through the keratin substrate.

DETAILED DESCRIPTION OF THE INVENTION

I. Definitions and Abbreviations

As used herein, the singular forms "a," "an", and "the" include plural references unless the context clearly dictates otherwise. For example, reference to "an active agent" includes a single active agent as well as two or more different active agents in combination. It is to be understood that present teaching is not limited to the specific dosage forms, carriers, or the like, disclosed herein and as such may vary.

The abbreviations used herein generally have their conventional meaning within the chemical and biological arts.

The following abbreviations have been used: Ac is acetyl; AcOH is acetic acid; ACTBr is cetyltrimethylammonium bromide; AIBN is azobisisobutyronitrile or 2,2 azobisisobutyronitrile; aq. is aqueous; Ar is aryl; $B_2pin_2$ is bis(pinacolato)diboron; Bn is, in general, benzyl [see Cbz for one example of an exception]; $(BnS)_2$ is benzyl disulfide; BnSH is benzyl thiol or benzyl mercaptan; BnBr is benzyl bromide; Boc is tert-butoxy carbonyl; $Boc_2O$ is di-tert-butyl dicarbonate; Bz is, in general, benzoyl; BzOOH is benzoyl peroxide; Cbz or Z is benzyloxycarbonyl or carboxybenzyl; $Cs_2CO_3$ is cesium carbonate; CSA is camphor sulfonic acid; CTAB is cetyltrimethylammonium bromide; Cy is cyclohexyl; DABCO is 1,4-diazabicyclo[2.2.2]octane; DCM is dichloromethane or methylene chloride; DHP is dihydropyran; DIAD is diisopropyl azodicarboxylate; DIEA or DIPEA is N,N-diisopropylethylamine; DMAP is 4-(dimethylamino) pyridine; DME is 1,2-dimethoxyethane; DMF is N,N-dimethylformamide; DMSO is dimethylsulfoxide; equiv or eq. is equivalent; EtOAc is ethyl acetate; EtOH is ethanol; $Et_2O$ is diethyl ether; EDCI is N-(3-dimethylaminopropyl)-N'-ethylcarbodiimide hydrochloride; ELS is evaporative light scattering; equiv or eq is equivalent; h is hours; HATU is O-(7-azabenzotriazol-1-yl)-N,N,N',N'-tetramethyluronium hexafluorophosphate; HOBt is N-hydroxybenzotriazole; HCl is hydrochloric acid; HPLC is high pressure liquid chromatography; ISCO Companion is automated flash chromatography equipment with fraction analysis by UV absorption available from Presearch; KOAc or AcOK is potassium acetate; $K_2CO_3$ is potassium carbonate; $LiAlH_4$ or LAH is lithium aluminum hydride; LDA is lithium diisopropylamide; LHMDS is lithium bis(trimethylsilyl) amide; KHMDS is potassium bis(trimethylsilyl) amide; LiOH is lithium hydroxide; m-CPBA is 3-chloroperoxybenzoic acid; MeCN or ACN is methyl cyanide or cyanomethane or ethanenitrile or acetonitrile which are all names for the same compound; MeOH is methanol; $MgSO_4$ is magnesium sulfate; mins or min is minutes; Mp or MP is melting point; $NaCNBH_3$ is sodium cyanoborohydride; NaOH is sodium hydroxide; $Na_2SO_4$ is sodium sulfate; NBS is N-bromosuccinimide; $NH_4Cl$ is ammonium chloride; NIS is N-iodosuccinimide; $N_2$ is nitrogen; NMM is N-methylmorpholine; n-BuLi is n-butyllithium; overnight is O/N; $PdCl_2(pddf)$ is 1,1'-Bis (diphenylphosphino) ferrocene]dichloropalladium(II); Pd/C is the catalyst known as palladium on carbon; $Pd_2(dba)_3$ is an organometallic catalyst known as tris(dibenzylideneacetone) dipalladium(0); Ra Ni or Raney Ni is Raney nickel; Ph is phenyl; PMB is p-methoxybenzyl; PrOH is 1-propanol; iPrOH is 2-propanol; $POCl_3$ is phosphorus chloride oxide; PTSA is para-toluene sulfonic acid; Pyr. or Pyr or Py as used herein means Pyridine; RT or rt or r.t. is room temperature; sat. is saturated; Si-amine or Si—$NH_2$ is amino-functionalized silica, available from SiliCycle; Si-pyr is pyridyl-functionalized silica, available from SiliCycle; TEA or $Et_3N$ is triethylamine; TFA is trifluoroacetic acid; $Tf_2O$ is trifluoromethanesulfonic anhydride; THF is tetrahydrofuran; TFAA is trifluoroacetic anhydride; THP is tetrahydropyranyl; TMSI is trimethylsilyl iodide; $H_2O$ is water; $diNO_2PhSO_2Cl$ is dinitrophenyl sulfonyl chloride; 3-F-4-$NO_2$-$PhSO_2Cl$ is 3-fluoro-4-nitrophenylsulfonyl chloride; 2-MeO-4-$NO_2$-$PhSO_2Cl$ is 2-methoxy-4-nitrophenylsulfonyl chloride; and $(EtO)_2POCH_2COOEt$ is a triethylester of phosphonoacetic acid known as triethyl phosphonoacetate.

"Compound of the invention," as used herein refers to the compounds discussed herein, salts (e.g. pharmaceutically acceptable salts), solvates and hydrates of these compounds.

"Keratin substrate," as used herein, refers to materials that contain keratin, such as a mammalian nail.

"Base coat nail polish" refers to a nail polish which is often applied directly to the nail as the first of additional coats of polish. A base coat can be the only coat of nail polish applied. The base coat can cover nail imperfections such as dents, chips or discoloration. Base coats often contain little to no pigments and can act as a protective antistain barrier between the nail and the nail color nail polish. In some embodiments, a base coat contains nitrocellulose at a lower amount than found in a nail color nail polish. In some embodiments, a base coat contains nitrocellulose at a lower amount than found in a top coat nail polish. In some embodiments, a base coat contains resin at a higher amount than found in a nail color nail polish. In some embodiments, a base coat contains resin at a higher amount than found in a top coat nail polish. In some embodiments, a base coat contains plasticizers at a lower amount than found in a nail color nail polish. In some embodiments, a base coat contains plasticizers at a lower amount than found in a top coat nail polish.

"Top coat nail polish" refers to a nail polish which is often applied on top of one or more coats of nail polish. A top coat can be the only coat of nail polish applied, and can be applied directly to the nail. In some embodiments, a top coat contains nitrocellulose at a higher amount than found in a nail color nail polish. In some embodiments, a top coat contains resin at a lower amount than found in a nail color nail polish. In some embodiments, a top coat contains plasticizers at a higher amount than found in a nail color nail polish.

"Nail color nail polish" refers to a nail polish which contains pigments. An example of a nail color nail polish is a home typical nail color nail polish. Another example of a nail color nail polish is a salon typical nail color nail polish.

II. Introduction

It has been discovered that delivery of a compound, such as a 5-halogen benzoxaborole, such as 5-fluoro-1,3-dihydro-1-hydroxy-2,1-benzoxaborole (tavaborole), through a mammalian nail can be increased by placing at least one additional layer of material over the mammalian nail before the application of the 5-halogen benzoxaborole to the mammalian nail. Increasing delivery through the mammalian nail increases the amount of the antifungal drug present at the site of the infection. Therefore, the inventions described herein improve the growth inhibition and/or killing of a fungus, which are present in, on or underneath (such as in the nail bed) a mammalian nail. The inventions described herein also improve the treatment or prevention of disease.

The invention also provides additional advantages. Presently there are no FDA-approved topical onychomycosis treatments in which the sufferer can wear nail polish while undergoing treatment. Doing so would significantly diminish or entirely ablate the effectiveness of the onychomycosis treatment. For example, ciclopirox requires debridement and frequent trimming of the nails to facilitate its rather limited penetration. Nail polish allows the onychomycosis sufferer to hide the unsightly aspects of the infection. The ability to wear nail polish while topically treating the disease would be a benefit to sufferers as it would reduce the psychosocial effects of the infection such as embarrassment and social withdrawal. The ability to wear nail polish while topically treating the disease also will increase patient compliance with the treatment as it will minimize disruption to the daily life of the sufferer. A topical treatment in which penetration of the antifungal drug through the nail was not significantly reduced by the presence of nail polish would be a substantial improvement over current treatment options. Demonstration of increased penetration of the antifungal drug in the presence of nail polish would be an even more substantial improvement over current treatment options.

In an aspect, the invention provides compositions and methods and kits described herein.

IIa. Compositions

In an aspect, the invention provides a composition comprising a) a first layer comprising a compound of the invention, and b) a second layer comprising a nail polish component. In an exemplary embodiment, the invention provides a composition comprising a) a first layer comprising a compound of the invention, and b) a second layer comprising a nail polish component which is hardened. In an exemplary embodiment, the invention provides a composition comprising a) a first layer comprising a compound of the invention, and b) a second layer comprising keratin and a nail polish component. In an exemplary embodiment, the invention provides a composition comprising a) a first layer comprising a compound of the invention, and b) a second layer comprising keratin and a nail polish component which is hardened.

In an aspect, the invention provides a composition comprising a) a first layer comprising a pharmaceutical formulation described herein, and b) a second layer comprising a nail polish component. In an exemplary embodiment, the invention provides a composition comprising a) a first layer comprising a pharmaceutical formulation described herein, and b) a second layer comprising a nail polish component which is hardened. In an exemplary embodiment, the invention provides a composition comprising a) a first layer comprising a pharmaceutical formulation described herein, and b) a second layer comprising keratin and a nail polish component. In an exemplary embodiment, the invention provides a composition comprising a) a first layer comprising a pharmaceutical formulation described herein, and b) a second layer comprising keratin and a nail polish component which is hardened.

In an exemplary embodiment, for a composition described herein, the compound of the invention is 5-fluoro-1,3-dihydro-1-hydroxy-2,1-benzoxaborole. In an exemplary embodiment, for a composition described herein, the compound of the invention is 5-chloro-1,3-dihydro-1-hydroxy-2,1-benzoxaborole. In an exemplary embodiment, for a composition described herein, the compound of the invention is 5-bromo-1,3-dihydro-1-hydroxy-2,1-benzoxaborole. In an exemplary embodiment, for a composition described herein, the compound of the invention is 5-iodo-1,3-dihydro-1-hydroxy-2,1-benzoxaborole. In an exemplary embodiment, for a composition described herein, the compound of the invention is a compound having a structure:

wherein $R^1$ is a halogen. In an exemplary embodiment, for a composition described herein, the compound of the invention is a triazole antifungal agent. In an exemplary embodiment, for a composition described herein, the compound of the invention is efinaconazole. In an exemplary embodiment, for a composition described herein, the compound of the invention is an imidazole antifungal agent. In an exemplary embodiment, for a composition described herein, the compound of the invention is luliconazole.

In an exemplary embodiment, for any of the compositions described herein, the second layer is a coated nail. In an exemplary embodiment, for any of the compositions described herein, the second layer is a coated nail which comprises keratin and a nail polish component.

In an exemplary embodiment, for any of the compositions described herein, the second layer is a coated nail. In an exemplary embodiment, for any of the compositions described herein, wherein the nail polish component is a film former. In an exemplary embodiment, for any of the compositions described herein, wherein the nail polish component is nitrocellulose. In an exemplary embodiment, wherein the film former is selected from the group consisting of acrylate copolymers of methyl methacrylate and hexyl methacrylate, adipic acid/neopentyl glycol/trimelitic anhydride copolymer and acetyl tributyl citrate.

In an exemplary embodiment, for any of the compositions described herein, wherein the nail polish component is a resin. In an exemplary embodiment, for any of the compositions described herein, wherein the nail polish component is a resin, and the resin is selected from the group consisting of toluene sulfonamide formaldehyde resin, copolymers polyvinyl acetate, and butyrate.

In an exemplary embodiment, for any of the compositions described herein, wherein the nail polish component is a plasticizer. In an exemplary embodiment, for any of the compositions described herein, the nail polish component is a plasticizer, which is selected from the group consisting of trimethyl pentanyl diisobutyrate, triphenyl phosphate, ethyl tosylamide, and camphor.

In a first aspect, the invention provides a composition comprising a) a first layer comprising a compound having a structure:

wherein $R^1$ is a halogen, or a salt, solvate, or hydrate thereof, and b) a second layer comprising a nail polish component. In an exemplary embodiment, the composition comprises a) a first layer comprising a compound having a structure:

wherein $R^1$ is a halogen, or a salt, solvate, or hydrate thereof, and b) a second layer comprises keratin and a nail polish component.

In an exemplary embodiment, the second layer is as described herein, and the first layer comprises a compound of the invention. In an exemplary embodiment, the second layer is as described herein, and the first layer comprises a compound described herein. In an exemplary embodiment, the second layer is as described herein, and the first layer comprises 5-fluoro-1,3-dihydro-1-hydroxy-2,1-benzoxaborole, or a salt, solvate, or hydrate thereof. In an exemplary embodiment, the second layer is as described herein, and the first layer comprises 5-chloro-1,3-dihydro-1-hydroxy-2,1-benzoxaborole, or a salt, solvate, or hydrate thereof. In an exemplary embodiment, the second layer is as described herein, and the first layer comprises 5-bromo-1,3-dihydro-1-hydroxy-2,1-benzoxaborole, or a salt, solvate, or hydrate thereof.

In an exemplary embodiment, the first layer and the second layer are as provided herein, and wherein the first layer is in contact with and overlays the second layer.

In an exemplary embodiment, the first layer comprises a compound having a structure:

wherein $R^1$ is a halogen, or a salt, solvate, or hydrate thereof, and b) a second layer comprising a film former and keratin. In an exemplary embodiment, the invention provides a composition comprising a) a first layer comprising a compound having a structure:

wherein $R^1$ is a halogen, or a salt, solvate, or hydrate thereof, and b) a second layer comprising nitrocellulose and keratin.

In an exemplary embodiment, the invention provides a composition comprising a) a first layer comprising a compound having a structure:

wherein $R^1$ is a halogen, or a salt, solvate, or hydrate thereof, and b) a second layer comprising a resin and keratin. In an exemplary embodiment, the invention provides a composition comprising a) a first layer comprising a compound having a structure:

wherein $R^1$ is a halogen, or a salt, solvate, or hydrate thereof, and b) a second layer comprising a tosylamide resin and keratin. In an exemplary embodiment, wherein the first layer is as described herein, and the second layer comprises a resin and keratin, and the resin is selected from the group consisting of toluene sulfonamide formaldehyde resin, copolymers polyvinyl acetate, and butyrate.

In an exemplary embodiment, the invention provides a composition comprising a) a first layer comprising a compound having a structure:

wherein $R^1$ is a halogen, or a salt, solvate, or hydrate thereof, and b) a second layer comprising a plasticizer and keratin. In an exemplary embodiment, wherein the first layer is as described herein, and the second layer comprises a plasticizer and keratin, and the plasticizer is selected from the group consisting of trimethyl pentanyl diisobutyrate, triphenyl phosphate, ethyl tosylamide, and camphor.

In an exemplary embodiment, the first layer is as described herein, and the second layer is as described herein, and the second layer further comprises cholesterol sulphate, ceramide, a sterol, a free fatty acid, a triglyceride, a sterol wax ester and squalene, or a combination thereof.

In an exemplary embodiment, wherein the second layer of the composition is as described herein, and the compound in the first layer is 5-fluoro-1,3-dihydro-1-hydroxy-2,1-benzoxaborole, or a salt thereof. In an exemplary embodiment, wherein the second layer of the composition is as described herein, and the compound in the first layer is 5-chloro-1,3-dihydro-1-hydroxy-2,1-benzoxaborole, or a salt thereof. In an exemplary embodiment, wherein the second layer of the composition is as described herein, and the compound in the first layer is 5-bromo-1,3-dihydro-1-hydroxy-2,1-benzoxaborole, or a salt thereof. In an exemplary embodiment, wherein the second layer of the composition is as described herein, and the compound in the first layer is 5-iodo-1,3-dihydro-1-hydroxy-2,1-benzoxaborole, or a salt thereof.

In an exemplary embodiment, wherein the second layer of the composition is as described herein, and the first layer is as described herein, and the first layer is a solution. In an exemplary embodiment, wherein the second layer of the composition is as described herein, and the first layer is as described herein, and the first layer is a simple solution. In an exemplary embodiment, wherein the second layer of the composition is as described herein, and the first layer is as described herein, and the first layer is an ointment. In an exemplary embodiment, wherein the second layer of the composition is as described herein, and the first layer is as described herein, and the first layer is a cream. In an exemplary embodiment, wherein the second layer of the composition is as described herein, and the first layer comprises propylene glycol and a compound of the invention.

In an exemplary embodiment, wherein the second layer of the composition is as described herein, and the first layer involves a solution comprising an alcohol and a compound of the invention. In an exemplary embodiment, wherein the second layer of the composition is as described herein, and the first layer involves a solution comprising an alcohol and a compound of the invention, and the alcohol is ethanol. In an exemplary embodiment, wherein the second layer of the composition is as described herein, and the first layer involves a solution comprising propylene glycol and a compound of the invention.

In an exemplary embodiment, the first layer is as described herein, and the second layer is as described herein, and the second layer does not comprise a compound of the invention. In an exemplary embodiment, the first layer is as described herein, and the second layer is as described herein, and the second layer does not comprise a compound having a structure:

wherein R¹ is a halogen, or a salt, solvate, or hydrate thereof. In an exemplary embodiment, the first layer is as described herein, and the second layer is as described herein, and the second layer does not comprise a compound which is 5-fluoro-1,3-dihydro-1-hydroxy-2,1-benzoxaborole. In an exemplary embodiment, the first layer is as described herein, and the second layer is as described herein, and the second layer does not comprise a compound which is 5-chloro-1,3-dihydro-1-hydroxy-2,1-benzoxaborole. In an exemplary embodiment, the first layer is as described herein, and the second layer is as described herein, and the second layer does not comprise a compound which is 5-bromo-1,3-dihydro-1-hydroxy-2,1-benzoxaborole. In an exemplary embodiment, the first layer is as described herein, and the second layer is as described herein, and the second layer does not comprise a compound which is an antifungal agent. In an exemplary embodiment, the first layer is as described herein, and the second layer is as described herein, and the second layer does not comprise a compound which is ciclopirox. In an exemplary embodiment, the first layer is as described herein, and the second layer is as described herein, and the second layer does not comprise a compound which is triazole antifungal agent. In an exemplary embodiment, the first layer is as described herein, and the second layer is as described herein, and the second layer does not comprise a compound which is efinaconazole. In an exemplary embodiment, the first layer is as described herein, and the second layer is as described herein, and the second layer does not comprise a compound which is an imidazole antifungal agent. In an exemplary embodiment, the first layer is as described herein, and the second layer is as described herein, and the second layer does not comprise a compound which is luliconazole.

In an exemplary embodiment, the second layer of the composition is as described herein, and the first layer of the composition comprises an alcohol. In an exemplary embodiment, the second layer of the composition is as described herein, and the first layer comprises methanol, ethanol, propanol, ethylene glycol, propylene glycol, and combinations thereof. In an exemplary embodiment, the composition of the invention further comprises a means for enhancing nail penetration. In an exemplary embodiment, the composition of the invention further comprises a means for enhancing nail penetration, and the means is a brush.

IIb. Methods

In another aspect, the invention provides a method described herein utilizing a composition described herein. In an exemplary embodiment, a method described herein utilizes a compound of the invention. In an exemplary embodiment, a method described herein utilizes a compound described herein. In an exemplary embodiment, a method described herein utilizes a pharmaceutical formulation described herein.

In an exemplary embodiment, for a method described herein, the compound of the invention is 5-fluoro-1,3-dihydro-1-hydroxy-2,1-benzoxaborole. In an exemplary embodiment, for a method described herein, the compound of the invention is 5-chloro-1,3-dihydro-1-hydroxy-2,1-benzoxaborole. In an exemplary embodiment, for a method described herein, the compound of the invention is 5-bromo-1,3-dihydro-1-hydroxy-2,1-benzoxaborole. In an exemplary embodiment, for a method described herein, the compound of the invention is 5-iodo-1,3-dihydro-1-hydroxy-2,1-benzoxaborole. In an exemplary embodiment, for a method described herein, the compound of the invention is a compound having a structure:

wherein R¹ is a halogen. In an exemplary embodiment, for a method described herein, the compound of the invention is a triazole antifungal agent. In an exemplary embodiment, for a method described herein, the compound of the invention is efinaconazole. In an exemplary embodiment, for a method described herein, the compound of the invention is an imidazole antifungal agent. In an exemplary embodiment, for a method described herein, the compound of the invention is luliconazole.

In an exemplary embodiment, the invention is a method of increasing the penetration of a compound of the invention through a keratin substrate, comprising: a) applying a nail polish to the keratin substrate, thus forming a coated nail; and b) applying the compound of the invention to the coated nail, thereby increasing the penetration of the compound of the invention through the keratin substrate.

In an exemplary embodiment, the invention is a method of increasing the penetration of a compound of the invention through a keratin substrate, comprising: a) applying a nail polish to the keratin substrate, thus forming a coated nail; and b) applying to the coated nail, a pharmaceutical formulation comprising the compound of the invention, thereby increasing the penetration of the compound of the invention through the keratin substrate.

In an exemplary embodiment, the invention is a method of inducing the penetration of a compound of the invention through a keratin substrate, comprising: a) applying a nail polish to the keratin substrate, thus forming a coated nail; and b) applying the compound of the invention to the coated nail, thereby inducing the penetration of the compound of the invention through the keratin substrate.

In an exemplary embodiment, the invention is a method of inducing the penetration of a compound of the invention through a keratin substrate, comprising: a) applying a nail polish to the keratin substrate, thus forming a coated nail; and b) applying to the coated nail, a pharmaceutical formulation comprising the compound of the invention, thereby inducing the penetration of the compound of the invention through the keratin substrate.

In an exemplary embodiment, the invention is a method of distributing a compound of the invention through a keratin substrate, comprising: a) applying a nail polish to the keratin substrate, thus forming a coated nail; and b) applying the compound of the invention to the coated nail, thereby distributing the compound of the invention through the keratin substrate.

In an exemplary embodiment, the invention is a method of distributing a compound of the invention through a keratin substrate, comprising: a) applying a nail polish to the keratin substrate, thus forming a coated nail; and b) applying to the coated nail, a pharmaceutical formulation comprising the compound of the invention, thereby distributing the compound of the invention through the keratin substrate.

In an exemplary embodiment, the invention is a method of delivering a compound of the invention through a keratin substrate, comprising: a) applying a nail polish to the keratin substrate, thus forming a coated nail; and b) applying the compound of the invention to the coated nail, thereby delivering the compound of the invention through the keratin substrate.

In an exemplary embodiment, the invention is a method of delivering a compound of the invention through a keratin substrate, comprising: a) applying a nail polish to the keratin substrate, thus forming a coated nail; and b) applying to the coated nail, a pharmaceutical formulation comprising the compound of the invention, thereby delivering the compound of the invention through the keratin substrate.

In an exemplary embodiment, the invention is a method of inhibiting the growth of a fungus, or killing a fungus, or both, and wherein the fungus is located on a keratin substrate, or within a keratin substrate, or underneath a keratin substrate, comprising: a) applying a nail polish to the keratin substrate, thus forming a coated nail; and b) applying a compound of the invention to the coated nail, thereby inhibiting the growth of a fungus, or killing a fungus, or both.

In an exemplary embodiment, the invention is a method of inhibiting the growth of a fungus, or killing a fungus, or both, and wherein the fungus is located on a keratin substrate, or within a keratin substrate, or underneath a keratin substrate, comprising: a) applying a nail polish to the keratin substrate, thus forming a coated nail; and b) applying to the coated nail, a pharmaceutical formulation comprising a compound of the invention, thereby inhibiting the growth of a fungus, or killing a fungus, or both.

In an exemplary embodiment, the invention is a method of inhibiting the growth of a fungus, or killing a fungus, or both, and wherein the fungus is located on a keratin substrate, or within a keratin substrate, or underneath a keratin substrate, comprising any combination of the applying a) and applying b) descriptions provided herein, thereby inhibiting the growth of a fungus, or killing a fungus, or both.

In an exemplary embodiment, the invention is a method of inhibiting the growth of a fungus, or killing a fungus, or both, and wherein the fungus is located on a keratin substrate, or within a keratin substrate, or underneath a keratin substrate, comprising any combination of the applying a) and waiting a1) and applying b) descriptions provided herein, thereby inhibiting the growth of a fungus, or killing a fungus, or both.

In an exemplary embodiment, the invention is a method of treating a disease in a mammal, comprising: a) applying a nail polish to the keratin substrate, thus forming a coated nail; and b) applying a compound of the invention to the coated nail, thereby treating the disease in the mammal.

In an exemplary embodiment, the invention is a method of preventing a disease in a mammal, comprising: a) applying a nail polish to the keratin substrate, thus forming a coated nail; and b) applying a compound of the invention to the coated nail, thereby preventing the disease in the mammal.

In an exemplary embodiment, the invention is a method of treating a disease in a mammal, comprising: a) applying a nail polish to the keratin substrate, thus forming a coated nail; and b) applying to the coated nail, a pharmaceutical formulation comprising a compound of the invention, thereby treating the disease in the mammal.

In an exemplary embodiment, the invention is a method of preventing a disease in a mammal, comprising: a) applying a nail polish to the keratin substrate, thus forming a coated nail; and b) applying to the coated nail, a pharmaceutical formulation comprising a compound of the invention, thereby preventing the disease in the mammal.

In an exemplary embodiment, the invention is a method of treating a disease in a mammal, comprising any combination of the applying a) and applying b) descriptions provided herein, thereby treating the disease in the mammal. In an exemplary embodiment, the invention is a method of preventing a disease in a mammal, comprising any combination of the applying a) and applying b) descriptions provided herein, thereby preventing the disease in the mammal.

In an exemplary embodiment, the invention is a method of treating a disease in a mammal, comprising any combination of the applying a) and waiting a1) and applying b) descriptions provided herein, thereby treating the disease in the mammal. In an exemplary embodiment, the invention is a method of preventing a disease in a mammal, comprising any combination of the applying a) and waiting a1) and applying b) descriptions provided herein, thereby preventing the disease in the mammal.

In an exemplary embodiment, for any of the methods or compositions described herein, the keratin substrate is a mammalian nail. In an exemplary embodiment, for any of the methods or compositions described herein, the keratin substrate is a human nail. In an exemplary embodiment, for any of the methods or compositions described herein, the keratin substrate is a human fingernail. In an exemplary embodiment, for any of the methods or compositions described herein, the keratin substrate is a human fingernail, and the human fingernail is a thumbnail. In an exemplary embodiment, for any of the methods or compositions described herein, the keratin substrate is a human toenail. In an exemplary embodiment, for any of the methods or compositions described herein, the keratin substrate is a mammalian nail, and the nail polish is applied to the dorsal side of the mammalian nail. In an exemplary embodiment, for any of the methods or compositions described herein, the keratin substrate is a mammalian nail, and the nail polish is applied to the dorsal side of the mammalian nail.

In an exemplary embodiment, for a method or composition or kit described herein, the compound is 5-fluoro-1,3-dihydro-1-hydroxy-2,1-benzoxaborole, or a salt, solvate or hydrate thereof. In an exemplary embodiment, for a method or composition or kit described herein, the compound is 5-chloro-1,3-dihydro-1-hydroxy-2,1-benzoxaborole, or a salt, solvate or hydrate thereof. In an exemplary embodiment, for a method or composition or kit described herein, the compound is 5-bromo-1,3-dihydro-1-hydroxy-2,1-benzoxaborole, or a salt, solvate or hydrate thereof. In an exemplary embodiment, for a method or composition or kit described herein, the compound is 5-iodo-1,3-dihydro-1-hydroxy-2,1-benzoxaborole, or a salt, solvate or hydrate thereof.

In an exemplary embodiment, for a method or composition or kit described herein, the nail polish is a top coat nail polish. In an exemplary embodiment, for a method or composition or kit described herein, the nail polish is a nail color nail polish. In an exemplary embodiment, the nail color nail polish is a home nail color nail polish. In an exemplary embodiment, the nail color nail polish is a salon nail color nail polish. In an exemplary embodiment, for a method or composition or kit described herein, the nail polish is a base coat nail polish.

In an exemplary embodiment, for a method or composition or kit described herein, the nail polish does not contain a compound of the invention. In an exemplary embodiment, for a method or composition or kit described herein, the nail polish at the beginning of the applying a) does not contain a compound of the invention. In an exemplary embodiment, for a method or composition or kit described herein, the coated nail before the applying b) does not contain a compound of the invention.

In an exemplary embodiment, for a method or composition or kit described herein, the nail polish does not contain ciclopirox. In an exemplary embodiment, for a method or composition or kit described herein, the nail polish at the beginning of the applying a) does not contain ciclopirox. In an exemplary embodiment, for a method or composition or kit described herein, the coated nail before the applying b) does not contain ciclopirox.

In an exemplary embodiment, for a method or composition or kit described herein, the nail polish does not contain 5-fluoro-1,3-dihydro-1-hydroxy-2,1-benzoxaborole. In an exemplary embodiment, for a method or composition or kit described herein, the nail polish at the beginning of the applying a) does not contain 5-fluoro-1,3-dihydro-1-hydroxy-2,1-benzoxaborole. In an exemplary embodiment, for a method or composition or kit described herein, the nail polish at the beginning of the applying a) does not contain 5-chloro-1,3-dihydro-1-hydroxy-2,1-benzoxaborole. In an exemplary embodiment, for a method or composition or kit described herein, the nail polish at the beginning of the applying a) does not contain 5-bromo-1,3-dihydro-1-hydroxy-2,1-benzoxaborole. In an exemplary embodiment, for a method or composition or kit described herein, the nail polish at the beginning of the applying a) does not contain 5-iodo-1,3-dihydro-1-hydroxy-2,1-benzoxaborole.

In an exemplary embodiment, for any of the methods described herein, further comprising, between the applying a) and the applying b), a1) waiting a period of time. In an exemplary embodiment, the waiting is until the nail polish hardens. In an exemplary embodiment, the waiting is until the nail polish partially hardens. In an exemplary embodiment, the waiting is until the nail polish at least partially hardens. In an exemplary embodiment, the waiting is until the nail polish dries. In an exemplary embodiment, the waiting is until the nail polish partially dries. In an exemplary embodiment, the waiting is until the nail polish at least partially dries. In an exemplary embodiment, the period of time is until the nail polish hardens. In an exemplary embodiment, the period of time is until the nail polish partially hardens. In an exemplary embodiment, the period of time is until the nail polish at least partially hardens. In an exemplary embodiment, the period of time is until the nail polish dries. In an exemplary embodiment, the period of time is until the nail polish partially dries. In an exemplary embodiment, the period of time is until the nail polish at least partially dries.

In an exemplary embodiment, for any of the methods described herein, further comprising, between the applying a) and the applying b), a1) waiting between about 0.5 seconds and about 3 days. In an exemplary embodiment, for any of the methods described herein, further comprising, between the applying a) and the applying b), a1) waiting between about 6 hours and about 2 days. In an exemplary embodiment, for any of the methods described herein, further comprising, between the applying a) and the applying b), a1) waiting between about 1 second and about 2 hours. In an exemplary embodiment, for any of the methods described herein, further comprising, between the applying a) and the applying b), a1) waiting between about 1 second and about 1 hour. In an exemplary embodiment, for any of the methods described herein, further comprising, between the applying a) and the applying b), a1) waiting between about 1 second and about 30 minutes. In an exemplary embodiment, for any of the methods described herein, further comprising, between the applying a) and the applying b), a1) waiting between about 1 second and about 15 minutes. In an exemplary embodiment, for any of the methods described herein, further comprising, between the applying a) and the applying b), a1) waiting between about 1 minute and about 15 minutes. In an exemplary embodiment, for any of the methods described herein, further comprising, between the applying a) and the applying b), a1) waiting between about 2 minutes and about 10 minutes. In an exemplary embodiment, for any of the methods described herein, further comprising, between the applying a) and the applying b), a1) waiting between about 2 minutes and about 5 minutes. In an exemplary embodiment, for any of the methods described herein, further comprising, between the applying a) and the applying b), a1) waiting between about 1 minute and about 7 minutes. In an exemplary embodiment, for any of the methods described herein, further comprising, between the applying a) and the applying b), a1) waiting between about 2 minutes and about 10 minutes. In an exemplary embodiment, for any of the methods described herein, further comprising, between the applying a) and the applying b), a1) waiting between about 1 second and about 2 minutes. In an exemplary embodiment, for any of the methods described herein, further comprising, between the applying a) and the applying b), a1) waiting between about 10 seconds and about 2 minutes.

In an exemplary embodiment, for any of the methods described herein, wherein the applying a) is performed two times in sequence before the applying b) is performed. In an exemplary embodiment, for any of the methods described herein, wherein the applying a) is performed three times in sequence before the applying b) is performed. In an exemplary embodiment, for any of the methods described herein, wherein the applying a) is performed four times in sequence before the applying b) is performed. In an exemplary embodiment, for any of the methods described herein, wherein the applying a) is performed between about two times and about ten times in sequence before the applying b) is performed. In an exemplary embodiment, for any of the methods described herein, wherein the nail polish in each step a) is independently selected from the group consisting of a base coat nail polish, a nail color nail polish, and a top coat nail polish.

In an exemplary embodiment, for any of the methods described herein, wherein the applying a) and the waiting a1) are performed two times in sequence before the applying b) is performed. In an exemplary embodiment, for any of the methods described herein, wherein the applying a) and the waiting a1) are performed three times in sequence before the applying b) is performed. In an exemplary embodiment, for any of the methods described herein, wherein the applying a) and the waiting a1) are performed four times in sequence before the applying b) is performed. In an exemplary embodiment, for any of the methods described herein, wherein the applying a) and the waiting a1) are performed between about two times and about ten times in sequence before the applying b) is performed. In an exemplary embodiment, for any of the methods described herein, wherein the nail polish in each step a) is independently selected from the group consisting of a base coat nail polish, a nail color nail polish, and a top coat nail polish.

In an exemplary embodiment, for any of the methods described herein, wherein the nail polish of step a) is applied to the dorsal side of the mammalian nail.

In an exemplary embodiment, for any of the methods described herein involving a fungus, wherein the fungus is selected from the group consisting of *Candida* species,

*Trichophyton* species, *Microsporium* species, *Aspergillus* species, *Cryptococcus* species, *Blastomyces* species, *Cocciodiodes* species, *Histoplasma* species, *Paracoccidioides* species, *Phycomycetes* species, *Malassezia* species, *Fusarium* species, *Epidermophyton* species, *Scytalidium* species, *Scopulariopsis* species, *Alternaria* species, *Penicillium* species, *Phialophora* species, *Rhizopus* species, *Scedosporium* species and *Zygomycetes* class. In an exemplary embodiment, for any of the methods described herein involving a fungus, wherein the fungus is a dermatophyte. In an exemplary embodiment, for any of the methods described herein involving a fungus, wherein the fungus is a *Trichophyton* species. In an exemplary embodiment, for any of the methods described herein involving a fungus, wherein the fungus is a *Microsporum* species. In an exemplary embodiment, for any of the methods described herein involving a fungus, wherein the fungus is an *Epidermophyton* species. In an exemplary embodiment, for any of the methods described herein involving a fungus, wherein the fungus is a yeast-like fungus. In an exemplary embodiment, for any of the methods described herein involving a fungus, wherein the fungus is *Trichophyton rubrum*. In an exemplary embodiment, for any of the methods described herein involving a fungus, wherein the fungus is *Trichophyton mentagrophytes*.

In an exemplary embodiment, for any of the methods described herein involving a disease, wherein the disease involves an infection. In an exemplary embodiment, for any of the methods described herein involving a disease, wherein the disease involves an infection, and the infection is an ungual infection. In an exemplary embodiment, for any of the methods described herein involving a disease, wherein the disease involves an infection, and the infection is a periungual infection. In an exemplary embodiment, for any of the methods described herein involving a disease, wherein the disease involves an infection, and the infection is a fungal infection.

In an exemplary embodiment, for any of the methods described herein involving a disease, wherein the disease is selected from the group consisting of chloronychia, paronychias, erysipeloid, onychorrhexis, gonorrhea, swimming-pool granuloma, larva migrans, leprosy, Orf nodule, milkers' nodules, herpetic whitlow, acute bacterial perionyxis, chronic perionyxis, sporotrichosis, syphilis, tuberculosis verrucosa cutis, tularemia, tungiasis, peri- and subungual warts, zona, nail dystrophy (trachyonychia), dermatological diseases, psoriasis, pustular psoriasis, alopecia aerata, parakeratosis pustulosa, contact dermatosis, Reiter's syndrome, psoriasiform acral dermatitis, lichen planus, idiopathy atrophy in the nails, lichin nitidus, lichen striatus, inflammatory linear verrucous epidermal naevus (ILVEN), alopecia, pemphigus, bullous pemphigoid, acquired epidermolysis bullosa, Darier's disease, *pityriasis rubra* pilaris, palmoplantar keratoderma, contact eczema, polymorphic erythema, scabies, Bazex syndrome, systemic scleroderma, systemic lupus erythematosus, chronic lupus erythematosus, dermatomyositus, Sporotrichosis, Mycotic keratitis, Extension oculomycosis, Endogenous oculomycosis, Lobomycosis, Mycetoma, *Piedra, Pityriasis versicolor*, Tinea corporis, Tinea cruris, Tinea pedis, Tinea barbae, Tinea capitis, Tinea nigra, Otomycosis, Tinea favosa, Chromomycosis, and Tinea Imbricata. In an exemplary embodiment, for any of the methods described herein involving a disease, wherein the disease is onychomycosis. In an exemplary embodiment, for any of the methods described herein involving a disease, wherein the disease is onychomycosis, and the onychomycosis is Tinea unguium. In an exemplary embodiment, for any of the methods described herein involving a mammal, wherein the mammal is selected from the group consisting of a human, cattle, goat, pig, sheep, horse, cow, bull, dog, guinea pig, gerbil, rabbit, and cat. In an exemplary embodiment, for any of the methods described herein involving a mammal, wherein the mammal is a human. In an exemplary embodiment, for any of the methods described herein involving a mammal, wherein the mammal is a dog. In an exemplary embodiment, for any of the methods described herein involving a mammal, wherein the mammal is a cat. In an exemplary embodiment, for any of the methods described herein involving a mammal, wherein the mammal is cattle. In an exemplary embodiment, for any of the methods described herein involving a mammal, wherein the mammal is selected from the group consisting of a cattle, goat, pig, sheep, and horse. In an exemplary embodiment, for any of the methods described herein involving a mammal, wherein the mammal is a cow or a bull.

In an exemplary embodiment, for any of the methods described herein involving an infection, wherein the infection is an ungual or periungual infection. In an exemplary embodiment, for any of the methods described herein involving an infection, wherein the infection is selected from the group consisting of chloronychia, paronychias, erysipeloid, onychorrhexis, gonorrhea, swimming-pool granuloma, larva migrans, leprosy, Orf nodule, milkers' nodules, herpetic whitlow, acute bacterial perionyxis, chronic perionyxis, sporotrichosis, syphilis, tuberculosis verrucosa cutis, tularemia, tungiasis, peri- and subungual warts, zona, nail dystrophy (trachyonychia), dermatological diseases, psoriasis, pustular psoriasis, alopecia aerata, parakeratosis pustulosa, contact dermatosis, Reiter's syndrome, psoriasiform acral dermatitis, lichen planus, idiopathy atrophy in the nails, lichin nitidus, lichen striatus, inflammatory linear verrucous epidermal naevus (ILVEN), alopecia, pemphigus, bullous pemphigoid, acquired epidermolysis bullosa, Darier's disease, *pityriasis rubra* pilaris, palmoplantar keratoderma, contact eczema, polymorphic erythema, scabies, Bazex syndrome, systemic scleroderma, systemic lupus erythematosus, chronic lupus erythematosus, dermatomyositus, Sporotrichosis, Mycotic keratitis, Extension oculomycosis, Endogenous oculomycosis, Lobomycosis, Mycetoma, *Piedra, Pityriasis versicolor*, Tinea corporis, Tinea cruris, Tinea pedis, Tinea barbae, Tinea capitis, Tinea nigra, Otomycosis, Tinea favosa, Chromomycosis, and Tinea Imbricata. In an exemplary embodiment, for any of the methods described herein involving an infection, wherein the infection is onychomycosis. In an exemplary embodiment, for any of the methods described herein involving an infection, wherein the infection is onychomycosis, and the onychomycosis is Tinea unguium. In an exemplary embodiment, for any of the methods described herein involving a mammal, wherein the mammal is selected from the group consisting of a human, cattle, goat, pig, sheep, horse, cow, bull, dog, guinea pig, gerbil, rabbit, and cat. In an exemplary embodiment, for any of the methods described herein involving a mammal, wherein the mammal is a human. In an exemplary embodiment, for any of the methods described herein involving a mammal, wherein the mammal is a dog. In an exemplary embodiment, for any of the methods described herein involving a mammal, wherein the mammal is a cat. In an exemplary embodiment, for any of the methods described herein involving a mammal, wherein the mammal is cattle. In an exemplary embodiment, for any of the methods described herein involving a mammal, wherein the mammal is selected from the group con-sisting of a cattle, goat, pig, sheep, and horse. In an exemplary embodiment, for any of the methods described herein involving a mammal, wherein the mammal is a cow or a bull.

In an exemplary embodiment, for any of the compositions described herein, the second layer is a coated nail. In an exemplary embodiment, for any of the compositions described herein, the second layer is a coated nail which comprises keratin and a nail polish component.

In an exemplary embodiment, a method or composition or kit described herein involves a compound described herein, or a salt, hydrate or solvate thereof, or a combination thereof. In an exemplary embodiment, a method or composition or kit described herein involves a compound described herein, or a salt, hydrate or solvate thereof. In an exemplary embodiment, a method or composition or kit described herein involves a compound described herein, or a salt thereof. In an exemplary embodiment, the salt is a pharmaceutically acceptable salt. In an exemplary embodiment, a method or composition or kit described herein involves a compound described herein, or a hydrate thereof. In an exemplary embodiment, a method or composition or kit described herein involves a compound described herein, or a solvate thereof. In an exemplary embodiment, a method or composition or kit described herein involves a compound described herein. In an exemplary embodiment, a method or composition or kit described herein involves a pharmaceutically acceptable salt of a compound described herein. In an exemplary embodiment, a method or composition or kit described herein involves a hydrate of a compound described herein. In an exemplary embodiment, a method or composition or kit described herein involves a solvate of a compound described herein.

IIc. Kits

Another aspect of the present invention relates to a kit useful for performing one or more of the methods described herein. In an exemplary embodiment, the kit comprises a compound of the invention. In an exemplary embodiment, the kit comprises a compound of the invention and a nail polish. In an exemplary embodiment, the kit comprises a compound of the invention and a nail polish described herein.

In an exemplary embodiment, the kit comprises a compound of the invention and instructions for using the kit. In an exemplary embodiment, the kit comprises a compound described herein and a nail polish and instructions for using the kit. In an exemplary embodiment, the kit comprises a compound described herein and a nail polish described herein and instructions for using the kit.

In an exemplary embodiment, the kit comprises a pharmaceutical formulation described herein. In an exemplary embodiment, the kit comprises a pharmaceutical formulation described herein and a nail polish. In an exemplary embodiment, the kit comprises a pharmaceutical formulation described herein and a nail polish described herein.

In an exemplary embodiment, the kit comprises a pharmaceutical formulation described herein and instructions for using the kit. In an exemplary embodiment, the kit comprises a pharmaceutical formulation described herein and a nail polish and instructions for using the kit. In an exemplary embodiment, the kit comprises a pharmaceutical formulation described herein and a nail polish described herein and instructions for using the kit.

In an exemplary embodiment, the kit comprises a composition described herein. In an exemplary embodiment, the kit comprises a composition described herein and a nail polish. In an exemplary embodiment, the kit comprises a composition described herein and a nail polish described herein.

In an exemplary embodiment, the kit comprises a composition described herein and instructions for using the kit. In an exemplary embodiment, the kit comprises a composition described herein and a nail polish and instructions for using the kit. In an exemplary embodiment, the kit comprises a composition described herein and a nail polish described herein and instructions for using the kit.

In an exemplary embodiment, for a kit described herein, the compound of the invention is 5-fluoro-1,3-dihydro-1-hydroxy-2,1-benzoxaborole. In an exemplary embodiment, for a kit described herein, the compound of the invention is 5-chloro-1,3-dihydro-1-hydroxy-2,1-benzoxaborole. In an exemplary embodiment, for a kit described herein, the compound of the invention is 5-bromo-1,3-dihydro-1-hydroxy-2,1-benzoxaborole. In an exemplary embodiment, for a kit described herein, the compound of the invention is 5-iodo-1,3-dihydro-1-hydroxy-2,1-benzoxaborole. In an exemplary embodiment, for a kit described herein, the compound of the invention is a compound having a structure:

wherein $R^1$ is a halogen. In an exemplary embodiment, for a kit described herein, the compound of the invention is a triazole antifungal agent. In an exemplary embodiment, for a kit described herein, the compound of the invention is efinaconazole. In an exemplary embodiment, for a kit described herein, the compound of the invention is an imidazole antifungal agent. In an exemplary embodiment, for a kit described herein, the compound of the invention is luliconazole.

III) Preparation of Compounds

Compounds of use in the invention can be prepared using commercially available starting materials, known intermediates, or by using the synthetic methods described herein, or published in references described and incorporated by reference herein, such as U.S. Prov. Pat. App. 60/654,060; Filed Feb. 16, 2005; U.S. patent application Ser. No. 11/357,687, Filed Feb. 16, 2006; U.S. patent application Ser. No. 11/505,591, Filed Aug. 16, 2006, U.S. Prov. Pat. App. 60/823,888 filed on Aug. 29, 2006 and 60/774,532 filed on Feb. 16, 2006; U.S. patent application Ser. No. 11/676,120, Filed Feb. 16, 2007; U.S. patent application Ser. No. 11/676,120, Filed Feb. 16, 2007; U.S. patent application Ser. No. 12/399,015, filed Mar. 5, 2009; U.S. patent application Ser. No. 13/015,487, filed Jan. 27, 2011, which are herein incorporated by reference in their entirety for all purposes. Methods of producing the compounds of the invention are also described in these patent applications. Some of the compounds of the invention can also be produced according to methods known to one of skill in the art.

Compounds described herein can be converted into hydrates and solvates by methods similar to those described herein.

IV) Pharmaceutical Formulation Information

In an exemplary embodiment, for a pharmaceutical formulation utilized in a composition or a method or a kit described herein, the pharmaceutical formulation comprises a) a pharmaceutically acceptable excipient; and b) a compound of the invention. In an exemplary embodiment, the pharmaceutically acceptable excipient is a compound described herein. In an exemplary embodiment, the pharmaceutically acceptable excipient is a compound described in this section. In an exemplary embodiment, for a pharmaceutical formulation described herein, the compound of the invention is 5-fluoro-1,3-dihydro-1-hydroxy-2,1-benzoxaborole. In an exemplary embodiment, for a pharmaceutical formulation described herein, the compound of the invention is 5-chloro-1,3-dihydro-1-hydroxy-2,1-benzoxaborole. In an exemplary embodiment, for a pharmaceutical formulation described herein, the compound of the invention is 5-bromo-1,3-dihydro-1-hydroxy-2,1-benzoxaborole. In an exemplary embodiment, for a pharmaceutical formulation described herein, the compound of the invention is 5-iodo-1,3-dihydro-1-hydroxy-2,1-benzoxaborole. In an exemplary embodiment, for a pharmaceutical formulation described herein, the compound of the invention is a compound having a structure:

wherein $R^1$ is a halogen. In an exemplary embodiment, for a pharmaceutical formulation described herein, the compound of the invention is a triazole antifungal agent. In an exemplary embodiment, for a pharmaceutical formulation described herein, the compound of the invention is efinaconazole. In an exemplary embodiment, for a pharmaceutical formulation described herein, the compound of the invention is an imidazole antifungal agent. In an exemplary embodiment, for a pharmaceutical formulation described herein, the compound of the invention is luliconazole.

A pharmaceutical formulation can comprise fluid or semisolid excipients that may include but are not limited to polymers, thickeners, buffers, neutralizers, chelating agents, preservatives, surfactants or emulsifiers, antioxidants, waxes or oils, emollients, sunscreens, and a solvent or mixed solvent system. In an exemplary embodiment, the pharmaceutically acceptable excipient is a solvent, and the solvent is an alcohol. In an exemplary embodiment, the pharmaceutically acceptable excipient is a solvent, and the solvent is an alcohol described herein. In an exemplary embodiment, the pharmaceutically acceptable excipient is a mixed solvent, and the mixed solvent comprises one or more alcohols. In an exemplary embodiment, the pharmaceutically acceptable excipient is a mixed solvent, and the mixed solvent comprises one or more alcohols described herein. The pharmaceutical formulations can be made into a wide variety of product types. These include, but are not limited to, lotions, creams, gels, sticks, sprays, ointments, pastes, foams, mousses, and cleansers. These pharmaceutical formulations can comprise several types of carrier systems including, but not limited to particles, nanoparticles, and liposomes. If desired, disintegrating agents can be added, such as the cross-linked polyvinyl pyrrolidone, agar or alginic acid or a salt thereof such as sodium alginate. Techniques for formulation and administration can be found in *Remington: The Science and Practice of Pharmacy*, supra.

Lotions, which are preparations that can be applied to the skin, nail, hair, claw or hoof surface without friction, are typically liquid or semi-liquid preparations in which finely divided solid, waxy, or liquid are dispersed. Lotions can contain suspending agents to produce better dispersions as well as compounds useful for localizing and holding the compound of the invention in contact with the skin, nail, hair, claw or hoof, e.g., methylcellulose, sodium carboxymethyl-cellulose, or the like.

Creams containing the compound of the invention for delivery according to the present invention are viscous liquid or semisolid emulsions, either oil-in-water or water-in-oil. Cream bases are water-washable, and contain an oil phase, an emulsifier and an aqueous phase. The oil phase is generally comprised of petrolatum or a fatty alcohol, such as cetyl- or stearyl alcohol; the aqueous phase usually, although not necessarily, exceeds the oil phase in volume, and generally contains a humectant. The emulsifier in a cream formulation, as explained in *Remington: The Science and Practice of Pharmacy*, supra, is generally a nonionic, anionic, cationic or amphoteric surfactant.

Gel formulations can also be used in connection with the present invention. As will be appreciated by those working in the field of topical drug formulation, gels are semisolid. Single-phase gels contain organic macromolecules distributed substantially uniformly throughout the carrier liquid, which is typically aqueous, but also may be a solvent or solvent blend.

Ointments, which are semisolid preparations, are typically based on petrolatum or other petroleum derivatives. As will be appreciated by the ordinarily skilled artisan, the specific ointment base to be used is one that provides for optimum delivery for the compound of the invention chosen for a given formulation, and can provide for other desired characteristics as well, e.g., emolliency or the like. As with other carriers or vehicles, an ointment base should be inert, stable, nonirritating and non-sensitizing. As explained in Remington: The Science and Practice of Pharmacy, 19th Ed. (Easton, Pa.: Mack Publishing Co., 1995), at pages 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Water-soluble ointment bases can be prepared from polyethylene glycols of varying molecular weight; again, reference may be had to Remington: The Science and Practice of Pharmacy, supra, for further information.

Useful formulations of the invention also encompass sprays. Sprays generally provide the compound of the invention in an aqueous and/or alcoholic solution which can be misted onto the skin, nail, hair, claw or hoof for delivery. Such sprays include those formulated to provide for concentration of the compound of the invention solution at the site of administration following delivery, e.g., the spray solution can be primarily composed of alcohol or other like volatile liquid in which the compound of the invention can be dissolved. Upon delivery to the skin, nail, hair, claw or hoof, the carrier evaporates, leaving concentrated compound of the invention at the site of administration.

The pharmaceutical formulation may also comprise suitable solid or gel phase carriers. Examples of such carriers include but are not limited to calcium carbonate, calcium phosphate, various sugars, starches, cellulose derivatives, gelatin, and polymers such as polyethylene glycols.

The pharmaceutical formulation may also comprise a suitable emulsifier which refers to an agent that enhances or facilitates mixing and suspending oil-in-water or water-in-oil. The emulsifying agent used herein may consist of a single emulsifying agent or may be a nonionic, anionic, cationic or amphoteric surfactant or blend of two or more such surfactants; such as nonionic or anionic emulsifiers. Such surface-active agents are described in "McCutcheon's Detergent and Emulsifiers," North American Edition, 1980 Annual published by the McCutcheon Division, MC Publishing Company, 175 Rock Road, Glen Rock, N.J. 07452, USA.

In an exemplary embodiment, high molecular weight alcohols such as cetearyl alcohol, cetyl alcohol, stearyl alcohol, emulsifying wax, glyceryl Monostearate can be employed in the pharmaceutical formulations. Other examples are ethylene glycol distearate, sorbitan tristearate, propylene glycol monostearate, sorbitan monooleate, sorbitan monostearate (SPAN 60), diethylene glycol monolaurate, sorbitan monopalmitate, sucrose dioleate, sucrose stearate (CRODESTA F-160), polyoxyethylene lauryl ether (BRIJ 30), polyoxyethylene (2) stearyl ether (BRIJ 72), polyoxyethylene (21) stearyl ether (BRIJ 721), polyoxyethylene monostearate (Myrj 45), polyoxyethylene sorbitan monostearate (TWEEN 60), polyoxyethylene sorbitan monooleate (TWEEN 80), polyoxyethylene sorbitan monolaurate (TWEEN 20) and sodium oleate. Cholesterol and cholesterol derivatives may also be employed in externally used emulsions and promote w/o emulsions.

Especially suitable nonionic emulsifying agents are those with hydrophile-lipophile balances (HLB) of about 3 to 6 for w/o system and 8 to 18 for o/w system as determined by the method described by Paul L. Lindner in "Emulsions and Emulsion", edited by Kenneth Lissant, published by Dekker, New York, N.Y., 1974, pages 188-190. In an exemplary embodiment, there is one or more nonionic surfactants that produce a system having HLB of about 8 to about 18.

Examples of such nonionic emulsifiers include but are not limited to "BRIJ 72", the trade name for a polyoxyethylene (2) stearyl ether having an HLB of 4.9; "BRIJ 721", the trade name for a polyoxyethylene (21) stearyl ether having an HLB of 15.5, "Brij 30", the trade name for polyoxyethylene lauryl ether having an HLB of 9.7; "Polawax", the trade name for emulsifying wax having an HLB of 8.0; "Span 60", the trade name for sorbitan monostearate having an HLB of 4.7; "Crodesta F-160", the trade name for sucrose stearate" having an HLB of 14.5. All of these materials are available from Ruger Chemicals Inc.; Croda; ICI Americas, Inc.; Spectrum Chemicals; and BASF. When the topical formulations of the present invention contain at least one emulsifying agent, each emulsifying agent is present in amount from about 0.5% (w/w) to about 2.5% (w/w), or from about 0.5% (w/w) to about 2.0% (w/w), or from about 1.0% (w/w) to about 1.8% (w/w).

The pharmaceutical formulation may also comprise suitable emollients. Emollients are materials used for the prevention or relief of dryness, as well as for the protection of the skin, nail, hair, claw or hoof. Useful emollients include, but are not limited to, cetyl alcohol, isopropyl myristate, stearyl alcohol, and the like. A wide variety of suitable emollients are known and can be used herein. See e.g., Sagarin, Cosmetics, Science and Technology, 2nd Edition, Vol. 1, pp. 32-43 (1972), and U.S. Pat. No. 4,919,934, to Deckner et al., issued Apr. 24, 1990, both of which are incorporated herein by reference in their entirety. These materials are available from Ruger Chemical Co, (Irvington, N.J.).

When the pharmaceutical formulation contains at least one emollient, each emollient is present in an amount from about 0.1% (w/w) to 15% (w/w), or from about 0.1% (w/w) to about 3.0% (w/w), or about 0.5% (w/w), about 1.0% (w/w), or 2.5% (w/w).

The pharmaceutical formulation may also comprise suitable antioxidants, substances known to inhibit oxidation. Antioxidants suitable for use in accordance with the present invention include, but are not limited to, butylated hydroxytoluene, ascorbic acid, sodium ascorbate, calcium ascorbate, ascorbic palmitate, butylated hydroxyanisole, 2,4,5-trihydroxybutyrophenone, 4-hydroxymethyl-2,6-di-tert-butylphenol, erythorbic acid, gum guaiac, propyl gallate, thiodipropionic acid, dilauryl thiodipropionate, tert-butylhydroquinone and tocopherols such as vitamin E, and the like, including pharmaceutically acceptable salts and esters of these compounds. In an exemplary embodiment, the antioxidant is butylated hydroxytoluene, butylated hydroxyanisole, propyl gallate, ascorbic acid, pharmaceutically acceptable salts or esters thereof, or mixtures thereof. In an exemplary embodiment, the antioxidant is butylated hydroxytoluene. These materials are available from Ruger Chemical Co, (Irvington, N.J.).

When the topical formulations of the present invention contain at least one antioxidant, the total amount of antioxidant present is from about 0.001% (w/w) to 0.5% (w/w), or from about 0.05% (w/w) to about 0.5% (w/w), or about 0.1% (w/w).

The pharmaceutical formulation may also comprise suitable preservatives. Preservatives are compounds added to a pharmaceutical formulation to act as an anti-microbial agent. Among preservatives known in the art as being effective and acceptable in parenteral formulations are benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. See, e.g., Wallhausser, K.-H., Develop. Biol. Standard, 24:9-28 (1974) (S. Krager, Basel). In an exemplary embodiment, the preservative is selected from methylparaben, propylparaben and mixtures thereof. These materials are available from Inolex Chemical Co (Philadelphia, Pa.) or Spectrum Chemicals.

When the pharmaceutical formulation contains at least one preservative, the total amount of preservative present is from about 0.01% (w/w) to about 0.5% (w/w), or from about 0.1% (w/w) to about 0.5% (w/w), or from about 0.03% (w/w) to about 0.15% (w/w).

The pharmaceutical formulation may also comprise suitable chelating agents to form complexes with metal cations that do not cross a lipid bilayer. Examples of suitable chelating agents include ethylene diamine tetraacetic acid (EDTA), ethylene glycol-bis(beta-aminoethyl ether)-N,N,N',N'-tetraacetic acid (EGTA) and 8-Amino-2-[(2-amino-5-methylphenoxy)methyl]-6-methoxyquinoline-N,N,N',N'-tetraacetic acid, tetrapotassium salt (QUIN-2). In an exemplary embodiment, the chelating agent is EDTA. In an exemplary embodiment, the chelating agent is citric acid. These materials are available from Sigma-Aldrich (St. Louis, Mo.).

When the pharmaceutical formulation contains at least one chelating agent, the total amount of chelating agent present is from about 0.005% (w/w) to 2.0% (w/w), or from about 0.05% (w/w) to about 0.5% (w/w), or about 0.1% (w/w).

The pharmaceutical formulation may also comprise suitable neutralizing agents used to adjust the pH of the formulation to within a pharmaceutically acceptable range. Examples of neutralizing agents include but are not limited to trolamine, tromethamine, sodium hydroxide, hydrochloric acid, citric acid, and acetic acid. Such materials are available from are available from Spectrum Chemicals (Gardena, Calif.).

When the pharmaceutical formulation contains at least one neutralizing agent, the total amount of neutralizing agent present is from about 0.1% (w/w) to about 10% (w/w), or from about 0.1% (w/w) to about 5.0% (w/w), or about 1.0% (w/w). The neutralizing agent is generally added in whatever amount is required to bring the formulation to the desired pH.

The pharmaceutical formulation may also comprise suitable viscosity increasing agents. These components are diffusible compounds capable of increasing the viscosity of a polymer-containing solution through the interaction of the agent with the polymer. CARBOPOL ULTREZ 10 may be used as a viscosity-increasing agent. These materials are available from Noveon Chemicals, Cleveland, Ohio.

When the pharmaceutical formulation contains at least one viscosity increasing agent, the total amount of viscosity increasing agent present is from about 0.25% (w/w) to about 5.0% (w/w), or from about 0.25% (w/w) to about 1.0% (w/w), or from about 0.4% (w/w) to about 0.6% (w/w).

The pharmaceutical formulation may also comprise suitable nail penetration enhancers. Examples of nail penetration enhancers include mercaptan compounds, sulfites and bisulfites, keratolytic agents and surfactants. Nail penetration enhancers suitable for use in the invention are described in greater detail in Malhotra et al., *J. Pharm. Sci.*, 91:2, 312-323 (2002), which is incorporated herein by reference in its entirety.

The pharmaceutical formulation may also comprise one or more suitable solvents. The ability of any solid substance (solute) to dissolve in any liquid substance (solvent) is dependent upon the physical properties of the solute and the solvent. When solutes and solvents have similar physical properties the solubility of the solute in the solvent will be the greatest. This gives rise to the traditional understanding that "like dissolves like." Solvents can be characterized in one extreme as non-polar, lipophilic oils, while in the other extreme as polar hydrophilic solvents. Oily solvents dissolve other non-polar substances by Van der Wals interactions while water and other hydrophilic solvents dissolve polar substances by ionic, dipole, or hydrogen bonding interactions. All solvents can be listed along a continuum from the least polar, i.e. hydrocarbons such as decane, to the most polar solvent being water. A solute will have its greatest solubility in solvents having equivalent polarity. Thus, for drugs having minimal solubility in water, less polar solvents will provide improved solubility with the solvent having polarity nearly equivalent to the solute providing maximum solubility. Most drugs have intermediate polarity, and thus experience maximum solubility in solvents such as propylene glycol or ethanol, which are significantly less polar than water. If the drug has greater solubility in propylene glycol (for example 8% (w/w)) than in water (for example 0.1% (w/w)), then addition of water to propylene glycol should decrease the maximum amount of drug solubility for the solvent mixture compared with pure propylene glycol. Addition of a poor solvent to an excellent solvent will decrease the maximum solubility for the blend compared with the maximum solubility in the excellent solvent.

Liquid forms, such as lotions suitable for topical administration, may include a suitable aqueous or nonaqueous vehicle with buffers, suspending and dispensing agents, thickeners, penetration enhancers, and the like. Solid forms such as creams or pastes or the like may include, for example, any of the following ingredients, water, oil, alcohol or grease as a substrate with surfactant, polymers such as polyethylene glycol, thickeners, solids and the like. Liquid or solid formulations may include enhanced delivery technologies such as liposomes, microsomes, microsponges and the like.

Additionally, the compounds can be delivered using a sustained-release system, such as semipermeable matrices of solid hydrophobic polymers containing the compound of the invention. Various sustained-release materials have been established and are well known by those skilled in the art.

Topical treatment regimens according to the practice of this invention comprise applying the composition directly to the skin, nail, hair, claw or hoof at the application site, from one to several times daily.

Formulations of the present invention can be used to treat, ameliorate or prevent conditions or symptoms associated with bacterial infections, acne, inflammation and the like.

In an exemplary embodiment, the methods of the invention can be used employed through the topical application of a compound of the invention or a composition described herein. In an exemplary embodiment, the topical application is to the mammalian nail.

In an exemplary embodiment, the pharmaceutical formulation is a simple solution. In an exemplary embodiment, the pharmaceutical formulation includes an alcohol. In an exemplary embodiment, the pharmaceutical formulation includes alcohol and water. In an exemplary embodiment, the alcohol is ethanol, ethylene glycol, propanol, propylene glycol, isopropanol or butanol. In another exemplary embodiment, the pharmaceutical formulation is selected from the group consisting of about 10% (w/w) propylene glycol and about 90% (w/w) ethanol; about 20% (w/w) propylene glycol and about 80% (w/w) ethanol; about 30% (w/w) propylene glycol and about 70% (w/w) ethanol; about 40% (w/w) propylene glycol and about 60% (w/w) ethanol; about 50% (w/w) propylene glycol and about 50% (w/w) ethanol; about 60% (w/w) propylene glycol and about 40% (w/w) ethanol; about 70% (w/w) propylene glycol and about 30% (w/w) ethanol; about 80% (w/w) propylene glycol and about 20% (w/w) ethanol; about 90% (w/w) propylene glycol and about 10% (w/w) ethanol.

In an exemplary embodiment, the pharmaceutical formulation is a lacquer. Please see Remington's, supra, for more information on the production of lacquers.

The following are examples of the pharmaceutical excipients that can be added to the pharmaceutical formulations of the present invention. The following agents are known compounds and are readily available commercially.

Vitamins include, but are not limited to, Vitamin B, Vitamin E, Vitamin A, Vitamin D, and the like and vitamin derivatives such as tazarotene, calcipotriene, tretinoin, adapalene and the like.

Sunscreens and or sunburn relief agents include, but are not limited to, PABA, jojoba, aloe, padimate-O, methoxycinnamates, proxamine HCl, lidocaine and the like. Sunless tanning agents include, but are not limited to, dihydroxyacetone (DHA).

In an exemplary embodiment, the pharmaceutical formulation comprises an agent that controls or modifies keratinization, including without limitation: tretinoin, tazarotene, and adapalene.

In such compositions an additional cosmetically or pharmaceutically effective agent, such as an anti-inflammatory agent, vitamin, anti-aging agent, sunscreen, and/or acne-treating agent, for example, is usually a minor component (from about 0.001% to about 20% by weight or from about 0.01% to about 10% by weight) with the remainder being various vehicles or carriers and processing aids helpful for forming the desired dosing form.

In an exemplary embodiment, the pharmaceutical formulation comprises an alcohol and a compound of the invention. In an exemplary embodiment, the pharmaceutical formulation comprises methanol and a compound of the invention. In an exemplary embodiment, the pharmaceutical formulation comprises ethanol and a compound of the invention. In an exemplary embodiment, the pharmaceutical formulation comprises propanol and a compound of the invention. In an exemplary embodiment, the pharmaceutical formulation comprises isopropanol and a compound of the invention. In an exemplary embodiment, the pharmaceutical formulation comprises butanol and a compound of the invention. In an exemplary embodiment, the pharmaceutical formulation comprises pentanol and a compound of the invention. In an exemplary embodiment, the pharmaceutical formulation comprises ethylene glycol and a compound of the invention. In an exemplary embodiment, the pharmaceutical formulation comprises propylene glycol and a compound of the invention. In an exemplary embodiment, the pharmaceutical formulation comprises butylene glycol and a compound of the invention.

In an exemplary embodiment, the compound of the invention is present in the pharmaceutical formulation in a concentration of between about 0.5% (w/w) and about 15% (w/w). In an exemplary embodiment, the compound of the invention is present in the pharmaceutical formulation in a concentration of between about 0.1% (w/w) to about 12.5% (w/w). In an exemplary embodiment, the compound of the invention is present in the pharmaceutical formulation in a concentration of between about 0.5% (w/w) and about 2% (w/w). In an exemplary embodiment, the compound of the invention is present in the pharmaceutical formulation in a concentration of between about 0.5% (w/w) and about 7% (w/w). In an exemplary embodiment, the compound of the invention is present in the pharmaceutical formulation in a concentration of between about 2% (w/w) and about 7% (w/w). In an exemplary embodiment, the compound of the invention is present in the pharmaceutical formulation in a concentration of between about 4% (w/w) and about 6% (w/w). In an exemplary embodiment, the compound of the invention is present in the pharmaceutical formulation in a concentration of between about 8% (w/w) and about 12% (w/w). In an exemplary embodiment, the compound of the invention is present in the pharmaceutical formulation in a concentration of between about 4% (w/w) and about 6% (w/w). In an exemplary embodiment, the compound of the invention is present in the pharmaceutical formulation in a concentration of between about 5% (w/w) and about 7% (w/w). In an exemplary embodiment, the compound of the invention is present in the pharmaceutical formulation in a concentration of between about 2% (w/w) and about 5% (w/w).

Information regarding excipients of use in the formulations of the invention can be found in *Remington: The Science and Practice of Pharmacy*, 21st Ed., Pharmaceutical Press (2011) which is incorporated herein by reference.

Figure 1:
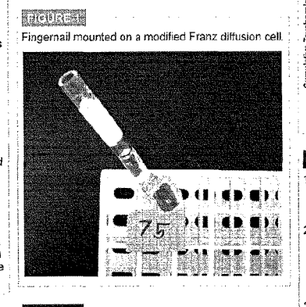
FIG. 1 provides additional information concerning the invention.
Figure 2:
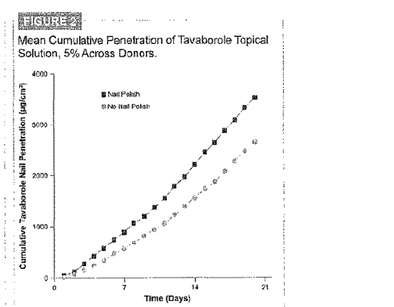

Additional information concerning the invention is provided in FIG. 1.

Exemplary embodiments are summarized herein below.

In a first aspect, the invention provides a method of delivering a compound through a keratin substrate, comprising: a) applying a nail polish to the keratin substrate, thus forming a coated nail; and b) applying to the coated nail, a pharmaceutical formulation comprising a pharmaceutically acceptable excipient and the compound, wherein the compound has the structure:

wherein $R^1$ is a halogen, or a pharmaceutically acceptable salt, solvate, or hydrate thereof, thereby delivering the compound through the keratin substrate.

In an exemplary embodiment, according to the above paragraph, the keratin substrate is a mammalian nail.

In an exemplary embodiment, according to any of the above paragraphs, the keratin substrate is a human nail.

In an exemplary embodiment, according to any of the above paragraphs, the nail polish is a top coat nail polish.

In an exemplary embodiment, according to any of the above paragraphs, the nail polish is a nail color nail polish.

In an exemplary embodiment, according to any of the above paragraphs, the nail polish is a base coat nail polish.

In an exemplary embodiment, according to any of the above paragraphs, the compound is 5-fluoro-1,3-dihydro-1-hydroxy-2,1-benzoxaborole, or a pharmaceutically acceptable salt, solvate, or hydrate thereof.

In an exemplary embodiment, according to any of the above paragraphs, the compound is 5-chloro-1,3-dihydro-1-hydroxy-2,1-benzoxaborole, or a pharmaceutically acceptable salt, solvate, or hydrate thereof.

In an exemplary embodiment, according to any of the above paragraphs, wherein at the beginning of the applying a) the nail polish does not contain the compound.

In another aspect, the invention provides a method of delivering a compound through a keratin substrate, comprising: a) applying a nail polish to the keratin substrate, thus forming a coated nail; a1) waiting for a period of time; b) applying to the coated nail, a pharmaceutical formulation comprising a pharmaceutically acceptable excipient and the compound, wherein the compound has the structure:

wherein $R^1$ is a halogen, or a pharmaceutically acceptable salt, solvate, or hydrate thereof, thereby delivering the compound through the keratin substrate.

In an exemplary embodiment, according to the above paragraph, the applying a) and the waiting a1) are performed twice in sequence before the applying b) is performed, and wherein the nail polish in each applying a) is independently selected from the group consisting of a base coat nail polish, a nail color nail polish, and a top coat nail polish.

In an exemplary embodiment, according to any of the above paragraphs, the applying a) and the waiting a1) are performed as a first applying a) and a first waiting a1) and a second applying a) and a second applying a1), and wherein the nail polish in the first applying a) is a base coat nail polish, and wherein the nail polish in the second applying a) is a nail color nail polish.

In an exemplary embodiment, according to any of the above paragraphs, the applying a) and the waiting a1) are performed as a first applying a) and a first waiting a1) and a second applying a) and a second applying a1), and wherein the nail polish in the first applying a) is a nail color nail polish, and wherein the nail polish in the second applying a) is a nail color nail polish.

In an exemplary embodiment, according to any of the above paragraphs, the applying a) and the waiting a1) are performed three times in sequence before the applying b) is performed, and wherein the nail polish in each step a) is independently selected from a base coat nail polish, a nail color nail polish, and a top coat nail polish.

In an exemplary embodiment, according to any of the above paragraphs, the applying a) and the waiting a1) are performed as a first applying a) and a first waiting a1) and a second applying a) and a second applying a1) and a third applying a) and a third waiting a1), and wherein the nail polish in the first applying a) is a base coat nail polish, and wherein the nail polish in the second applying a) is a nail color nail polish, and wherein the nail polish in the third applying a) is a top coat nail polish.

In an exemplary embodiment, according to any of the above paragraphs, the applying a) and the waiting a1) are performed four times in sequence before the applying b) is performed, and wherein the nail polish in each step a) is independently selected from a base coat nail polish, a nail color nail polish, and a top coat nail polish.

In an exemplary embodiment, according to any of the above paragraphs, the applying a) and the waiting a1) are performed as a first applying a) and a first waiting a1) and a second applying a) and a second applying a1) and a third applying a) and a third waiting a1) and a fourth applying a) and a fourth applying a1), and wherein the nail polish in the first applying a) is a base coat nail polish, and wherein the nail polish in the second applying a) is a nail color nail polish, and wherein the nail polish in the third applying a) is a nail color nail polish, and wherein the nail polish in the fourth applying a) is a top coat nail polish.

In an exemplary embodiment, according to any of the above paragraphs, the waiting is between about 1 second and about 10 minutes.

In an exemplary embodiment, according to any of the above paragraphs, the waiting is between about 30 seconds and about 5 minutes.

In an exemplary embodiment, according to any of the above paragraphs, the keratin substrate is a mammalian nail.

In an exemplary embodiment, according to any of the above paragraphs, the keratin substrate is a human nail.

In an exemplary embodiment, according to any of the above paragraphs, the nail polish is a top coat nail polish.

In an exemplary embodiment, according to any of the above paragraphs, the nail polish is a nail color nail polish.

In an exemplary embodiment, according to any of the above paragraphs, the nail polish is a base coat nail polish.

In an exemplary embodiment, according to any of the above paragraphs, wherein at the beginning of the applying a) the nail polish does not contain the compound.

In an exemplary embodiment, according to any of the above paragraphs, wherein at the beginning of each applying a) the nail polish does not contain the compound.

In an exemplary embodiment, according to any of the above paragraphs, wherein the compound is 5-fluoro-1,3-dihydro-1-hydroxy-2,1-benzoxaborole, or a pharmaceutically acceptable salt, solvate, or hydrate thereof.

In an exemplary embodiment, according to any of the above paragraphs, wherein the compound is 5-chloro-1,3-dihydro-1-hydroxy-2,1-benzoxaborole, or a pharmaceutically acceptable salt, solvate, or hydrate thereof.

In an exemplary embodiment, according to any of the above paragraphs, wherein the nail polish of the applying a) is applied to the dorsal side of the mammalian nail.

In another aspect, the invention provides a method of inhibiting the growth of a fungus, or killing a fungus, or both, and said fungus is located inside of a mammalian nail, or on the dorsal side of a mammalian nail, or on the proximal side of a mammalian nail, or on the nail bed, comprising: a) applying a nail polish to the mammalian nail, thus forming a coated nail; b) applying to the coated nail, a pharmaceutical formulation comprising a pharmaceutically acceptable excipient and the compound, wherein the compound has the structure:

wherein $R^1$ is a halogen, or a pharmaceutically acceptable salt, solvate, or hydrate thereof, thereby inhibiting the growth of a fungus, or killing a fungus, or both.

In an exemplary embodiment, according to the above paragraph, the fungus is selected from the group consisting of *Candida* species, *Trichophyton* species, *Microsporium* species, *Aspergillus* species, *Cryptococcus* species, *Blastomyces* species, *Cocciodiodes* species, *Histoplasma* species, *Paracoccidioides* species, *Phycomycetes* species, *Malassezia* species, *Fusarium* species, *Epidermophyton* species, *Scytalidium* species, *Scopulariopsis* species, *Alternaria* species, *Penicillium* species, *Phialophora* species, *Rhizopus* species, *Scedosporium* species and *Zygomycetes* class.

In an exemplary embodiment, according to any of the above paragraphs, the fungus is a dermatophyte.

In an exemplary embodiment, according to any of the above paragraphs, the fungus is selected from the group consisting of *Trichophyton* species, *Microsporum* species, and *Epidermophyton* species.

In an exemplary embodiment, according to any of the above paragraphs, the fungus is a yeast-like fungus.

In an exemplary embodiment, according to any of the above paragraphs, the fungus is *Trichophyton rubrum*.

In an exemplary embodiment, according to any of the above paragraphs, fungus is *Trichophyton mentagrophytes*.

In an exemplary embodiment, according to any of the above paragraphs, at the beginning of the applying a) the nail polish does not contain the compound.

In an exemplary embodiment, according to any of the above paragraphs, the compound is 5-fluoro-1,3-dihydro-1-hydroxy-2,1-benzoxaborole, or a pharmaceutically acceptable salt, solvate, or hydrate thereof.

In an exemplary embodiment, according to any of the above paragraphs, the compound is 5-chloro-1,3-dihydro-1-hydroxy-2,1-benzoxaborole, or a pharmaceutically acceptable salt, solvate, or hydrate thereof.

In an exemplary embodiment, according to any of the above paragraphs, the nail polish of the applying a) is applied to the dorsal side of the mammalian nail.

In another aspect, the invention provides a method of treating or preventing a disease in a mammal, comprising: a) applying a nail polish to the mammalian nail, thus forming a coated nail; b) applying to the coated nail, a pharmaceutical formulation comprising a pharmaceutically acceptable excipient and the compound, wherein the compound has the structure:

wherein $R^1$ is a halogen, or a pharmaceutically acceptable salt, solvate, or hydrate thereof, thereby treating or preventing the disease.

In an exemplary embodiment, according to the above paragraph, at the beginning of the applying a) the nail polish does not contain the compound.

In an exemplary embodiment, according to any of the above paragraphs, the disease is an infection.

In an exemplary embodiment, according to any of the above paragraphs, the disease is selected from the group consisting of chloronychia, paronychias, erysipeloid, onychorrhexis, gonorrhea, swimming-pool granuloma, larva migrans, leprosy, Orf nodule, milkers' nodules, herpetic whitlow, acute bacterial perionyxis, chronic perionyxis, sporotrichosis, syphilis, tuberculosis verrucosa cutis, tularemia, tungiasis, peri- and subungual warts, zona, nail dystrophy (trachyonychia), dermatological diseases, psoriasis, pustular psoriasis, alopecia aerata, parakeratosis pustulosa, contact dermatosis, Reiter's syndrome, psoriasiform acral dermatitis, lichen planus, idiopathy atrophy in the nails, lichin nitidus, lichen striatus, inflammatory linear verrucous epidermal naevus (ILVEN), alopecia, pemphigus, bullous pemphigoid, acquired epidermolysis bullosa, Darier's disease, *pityriasis rubra* pilaris, palmoplantar keratoderma, contact eczema, polymorphic erythema, scabies, Bazex syndrome, systemic scleroderma, systemic lupus erythematosus, chronic lupus erythematosus, dermatomyositus, Sporotrichosis, Mycotic keratitis, Extension oculomycosis, Endogenous oculomycosis, Lobomycosis, Mycetoma, *Piedra, Pityriasis versicolor*, Tinea corporis, Tinea cruris, Tinea pedis, Tinea barbae, Tinea capitis, Tinea nigra, Otomycosis, Tinea favosa, Chromomycosis, and Tinea Imbricata.

In an exemplary embodiment, according to any of the above paragraphs, the disease is onychomycosis.

In an exemplary embodiment, according to any of the above paragraphs, the disease is onychomycosis and said onychomycosis is Tinea unguium.

In an exemplary embodiment, according to any of the above paragraphs, the mammal is selected from the group consisting of human, cattle, goat, pig, sheep, horse, dog, rabbit, and cat.

In an exemplary embodiment, according to any of the above paragraphs, the mammal is a human.

In an exemplary embodiment, according to any of the above paragraphs, the compound is 5-fluoro-1,3-dihydro-1-hydroxy-2,1-benzoxaborole, or a pharmaceutically acceptable salt, solvate, or hydrate thereof.

In an exemplary embodiment, according to any of the above paragraphs, the compound is 5-chloro-1,3-dihydro-1-hydroxy-2,1-benzoxaborole, or a pharmaceutically acceptable salt, solvate, or hydrate thereof.

In an exemplary embodiment, according to any of the above paragraphs, the compound is 5-chloro-1,3-dihydro-1-hydroxy-2,1-benzoxaborole, or a pharmaceutically acceptable salt, solvate, or hydrate thereof.

In another aspect, the invention provides a composition comprising: a) a first layer comprising: a compound having the structure wherein $R^1$ is a halogen, or a pharmaceutically acceptable salt, solvate, or hydrate thereof, b) a coated nail comprising: keratin and a nail polish component, wherein the first layer is in contact with and overlays the coated nail.

In an exemplary embodiment, according to the above paragraph, the compound is not present in the coated nail.

In an exemplary embodiment, according to any of the above paragraphs, the nail polish component is a film former or a resin or a plasticizer.

In an exemplary embodiment, according to any of the above paragraphs, the nail polish component is nitrocellulose.

In an exemplary embodiment, according to any of the above paragraphs, the compound is 5-fluoro-1,3-dihydro-1-hydroxy-2,1-benzoxaborole, or a pharmaceutically acceptable salt, solvate, or hydrate thereof.

In an exemplary embodiment, according to any of the above paragraphs, the compound is 5-chloro-1,3-dihydro-1-hydroxy-2,1-benzoxaborole, or a pharmaceutically acceptable salt, solvate, or hydrate thereof.

In another aspect, the invention provides a kit comprising a composition according to any of the above paragraphs and instructions for using the composition.

In another aspect, the invention provides a kit comprising: a compound which is 5-fluoro-1,3-dihydro-1-hydroxy-2,1-benzoxaborole, or a pharmaceutically acceptable salt, solvate, or hydrate thereof, and instructions for using the compound according to any of the above paragraphs.

In another aspect, the invention provides a kit comprising: a pharmaceutical formulation comprising: a pharmaceutically acceptable excipient, and a compound which is 5-fluoro-1,3-dihydro-1-hydroxy-2,1-benzoxaborole, or a pharmaceutically acceptable salt, solvate, or hydrate thereof, and instructions for using the compound according to a method of any of the above paragraphs.

In an exemplary embodiment, according to any of the above paragraphs, the mammal is a human.

In an exemplary embodiment, according to any of the above paragraphs, the mammal is a human.

In an exemplary embodiment, according to any of the above paragraphs, the mammal is in need of treatment.

In an exemplary embodiment, according to any of the above paragraphs, the mammal is not already in need of treatment by the compound.

In an exemplary embodiment, according to any of the above paragraphs, the invention is a use of a compound described herein or a hydrate, solvate, or salt thereof, or a pharmaceutical formulation described herein in the manufacture of a medicament for the treatment and/or prevention of a disease.

The invention is further illustrated by the Examples that follow. The Examples are not intended to define or limit the scope of the invention.

EXAMPLES

The following Examples illustrate the synthesis of representative compounds used in the invention and the following Reference Examples illustrate the synthesis of intermediates in their preparation. These examples are not intended, nor are they to be construed, as limiting the scope of the invention. It will be clear that the invention may be practiced otherwise than as particularly described herein. Numerous modifications and variations of the invention are possible in view of the teachings herein and, therefore, are within the scope of the invention.

Example 1

Tavaborole Penetration of Fingernails with and without One Layer of Nail Polish

Female human ex vivo, cadaver fingernails, from four donors were cleaned of any underlying tissue, rinsed with water to remove any additional materials from the surface and then characterized for width, length, thickness, and weight. Two treatment groups were used to evaluate nail penetration of Tavaborole Topical Solution, 5% through nail polish. A third treatment group was the control group in which the nails were unpainted and not dosed with the Tavaborole Topical Solution.

In the first treatment group, eight nails, two nails from each of four donors, were painted with one coat of home typical nail color nail polish, Devil Wears Red #420, Lot No. J500, from L'Oreal. Nails in the first treatment group were painted on the day preceding the first dose of Tavaborole Topical Solution to ensure that the nail polish application was completely dry In the second treatment group, eight nails, two nails from each of the four donors, received no nail polish.

In the third treatment group, four nails were used, one nail from each of the four donors.

The nails were mounted on 7 mm diameter modified Franz diffusion cells and secured in place with silicone sealant. When the silicone sealant had appropriately solidified, prior to dosing, the receptor compartment of each diffusion cell was filled with distilled de-ionized water (ddH$_2$O) and inverted to test for leaks. The Franz cells were then filled with receiving medium phosphate buffered saline (PBS) (pH 7.4) and placed in a water bath set to achieve a nail surface temperature of 32±1.0° C.

Following collection of a pre-dose sample, each cell (except for the third treatment group) was dosed with approximately 12.5 µL/cm$^2$ of Tavabole Topical Solution, 5% by pipette to each cell, for twenty consecutive days. Within 24 hours of each dose, the receiving medium from each cell was removed in entirety and replaced with fresh solution. Prior to each subsequent daily dose, the nails were cleaned with a cotton swab moistened with water. Approximately 2 mL of each receiving medium sample was aliquoted into 8 mL vials, frozen, and then shipped for analysis by LC/MS/MS. The remaining samples were stored at −20° C.

Results

The mean cumulative penetration after twenty days of dosing of tavaborole from Tavaborole Topical Solution, 5% through painted nails was 3526±1433 µg/cm$^2$.

The mean cumulative penetration after twenty days of dosing of tavaborole from Tavaborole Topical Solution, 5% through unpainted nails was 2661±1319 µg/cm$^2$.

Although numerically superior, penetration of Tavaborole Topical Solution, 5% through nails with nail polish was not statistically different from penetration through nails without nail polish. These results demonstrate that Tavaborole Topical Solution, 5% was able to penetrate through one coat of a commercial brand of nail polish.

FIG. 1 provides additional information concerning the invention.

Example 2

Tavaborole Penetration of Fingernails with One, Two, or Four Layers of Nail Polish Female human ex vivo, cadaver fingernails from eight donors were cleaned of any underlying tissue, rinsed with water to remove any additional materials from the surface and then characterized for width, length, thickness, and weight. Four different treatment groups were used to evaluate different nail polish application practices. In the first treatment group, one nail from each of seven donors (randomized to treatment group) was painted according to the first nail polish application practice. In the second treatment group, a second nail from each of seven donors (randomized to treatment group) was painted according to the second nail polish application practice. In the third treatment group, a third nail from each of seven donors (randomized to treatment group) was painted according to the third nail polish application practice. In the fourth treatment group, a fourth nail from each of seven donors (randomized to treatment group) was painted according to the fourth nail polish application practice.

The first nail polish application practice painted the nails of the first treatment group with a nail polish base coat from L'Oreal, One Stop Base #200, Lot No. K700, followed by two coats of nail color nail polish. This nail color nail polish was a salon typical nail polish, Cocoa a Gogo, Lot No. 12228AB6, from Nicole by OPI Classic Shade. Finally, the nails were painted with a clear top coat nail polish from L'Oreal, Top of the Line #210, Lot No. K600.

The second nail polish application practice painted the nails of the second treatment group with one coat of a nail color nail polish. This nail color nail polish was a salon typical nail polish, Cocoa a Gogo, Lot No. 12228AB6, from Nicole by OPI Classic Shade.

The third nail polish application practice painted the nails of the third treatment group with two coats of nail color nail polish. This nail color nail polish was a home typical nail polish, Devil Wears Red #420, Lot No. J500, from L'Oreal.

The fourth nail polish application practice painted the nails of the fourth treatment group with one coat of a nail color nail polish. This nail color nail polish was a home typical nail polish, Devil Wears Red #420, Lot No. J500, from L'Oreal.

The nail polish was dried before applying each subsequent coat. Nails were painted on the day preceding the first dose to ensure that the nail polish applications were completely dry. Dry nails were re-weighed prior to mounting securely in individual nail adapters.

All nails were dosed with Tavaborole Topical Solution, 5%. No nails were used as non-dosed controls.

Vertical diffusion cells were filled with pre-warmed receiving medium of phosphate buffered saline (pH 7.4) and a small stir bar, and were allowed to equilibrate to 32±1.0° C. The cell volumes were determined prior to initiating the study. The nail adapters were then mounted on each cell, and the cells were fully assembled. Prior to dosing, each cell was evaluated for leaks. Following collection of a pre-dose sample, each cell was dosed with approximately 25 μL/cm$^2$ of Tavaborole Topical Solution, 5% by pipette to each cell, for fourteen consecutive days. Within 24 hours of each dose, the receiving medium from each cell was removed in entirety and replaced with fresh solution. Prior to each subsequent daily dose, the nails were cleaned with a cotton swab moistened with water. Approximately 4 mL of each receiving medium sample was aliquoted into 8 mL vials, frozen, and then shipped to Anacor for analysis by HPLC. The remaining samples were stored at −20° C.

Results:

After fourteen days of dosing with Tavaborole Topical Solution, 5%, the mean cumulative penetration through the nails subjected to the first nail polish application practice was 1178.527±554.399 μg/cm$^2$. After fourteen days of dosing with Tavaborole Topical Solution, 5%, the mean cumulative penetration through the nails subjected to the second nail polish application practice was 1227.300±974.002 μg/cm$^2$. After fourteen days of dosing with Tavaborole Topical Solution, 5%, the mean cumulative penetration through the nails subjected to the third nail polish application practice was 1492.517±1322.088 μg/cm$^2$. After fourteen days of dosing with Tavaborole Topical Solution, 5%, the mean cumulative penetration through the nails subjected to the fourth nail polish application practice was 1428.187±840.816 μg/cm$^2$. After fourteen days of dosing with Tavaborole Topical Solution, 5%, the mean cumulative penetration through the nails subjected to the control group application practice was 565.909±317.756 μg/cm$^2$.

Tavaborole was able to penetrate from Tavaborole Topical Solution, 5% through up to four layers of nail polish.

FIG. 1 provides additional information concerning the invention.

It is understood that the examples and embodiments described herein are for illustrative purposes only and that various modifications or changes in light thereof will be suggested to persons skilled in the art and are to be included within the spirit and purview of this application and scope of the appended claims. It is to be understood that the present invention covers all combinations of aspects and/or embodiments, as well as suitable, convenient and preferred groups described herein. All publications, patents, and patent applications cited herein are hereby incorporated by reference in their entirety for all purposes.

What is claimed is:

1. A method of inhibiting the growth of a fungus, or killing a fungus, or both, and said fungus is located inside of a mammalian nail, or on the dorsal side of a mammalian nail, or on the proximal side of a mammalian nail, or on the nail bed, comprising:
   a) applying a nail polish to the mammalian nail, thus forming a coated nail;
   b) applying to the coated nail, a pharmaceutical formulation comprising a pharmaceutically acceptable excipient and a compound, wherein the compound is 5-fluoro-1,3-dihydro-1-hydroxy-2,1-benzoxaborole or a pharmaceutically acceptable salt, solvate, or hydrate thereof thereby inhibiting the growth of a fungus, or killing a fungus, or both.

2. The method of claim 1, wherein the fungus is selected from the group consisting of *Candida* species, *Trichophyton* species, *Microsporum* species, *Aspergillus* species, *Cryptococcus* species, *Blastomyces* species, *Cocciodiodes* species, *Histoplasma* species, *Paracoccidioides* species, *Phycomycetes* species, *Malassezia* species, *Fusarium* species, *Epidermophyton* species, *Scytalidium* species, *Scopulariopsis* species, *Alternaria* species, *Penicillium* species, *Phialophora* species, *Rhizopus* species, *Scedosporium* species and *Zygomycetes* class.

3. The method of claim 1, wherein said fungus is a dermatophyte.

4. The method of claim 1, wherein said fungus is selected from the group consisting of *Trichophyton* species, *Microsporum* species, and *Epidermophyton* species.

5. The method of claim 1, wherein said fungus is a yeast-like fungus.

6. The method of claim 1, wherein said fungus is *Trichophyton rubrum*.

7. The method of claim 1, wherein said fungus is *Trichophyton mentagrophytes*.

8. The method of claim 1, wherein at the beginning of the applying a) the nail polish does not contain the compound.

9. The method of claim 1, wherein the nail polish of the applying a) is applied to the dorsal side of the mammalian nail.

* * * * *